US010066012B2

(12) United States Patent
Teeling et al.

(10) Patent No.: US 10,066,012 B2
(45) Date of Patent: *Sep. 4, 2018

(54) HUMAN MONOCLONAL ANTIBODIES AGAINST INTERLEUKIN 8 (IL-8)

(71) Applicant: CORMORANT PHARMACEUTICALS AB, Solna (SE)

(72) Inventors: Jessica Teeling, Krommenie (NL); Paul Parren, Utrecht (NL); Ole Baadsgaard, Hellerup (DK); Debra Hudson, Livermore, CA (US); Jørgen Petersen, Rungsted Kyst (DK)

(73) Assignee: CORMORANT PHARMACEUTICALS AB, Solna (SE)

( * ) Notice: Subject to any disclaimer, the term of this patent is extended or adjusted under 35 U.S.C. 154(b) by 256 days.

This patent is subject to a terminal disclaimer.

(21) Appl. No.: 15/138,490

(22) Filed: Apr. 26, 2016

(65) Prior Publication Data

US 2016/0280780 A1   Sep. 29, 2016
US 2017/0190770 A2   Jul. 6, 2017
US 2017/0334984 A9   Nov. 23, 2017
US 2018/0134783 A9   May 17, 2018

Related U.S. Application Data

(60) Continuation of application No. 14/074,226, filed on Nov. 7, 2013, which is a division of application No. 13/337,798, filed on Dec. 27, 2011, now Pat. No. 8,603,469, which is a division of application No. 12/616,615, filed on Nov. 11, 2009, now Pat. No. 8,105,588, which is a continuation of application No. 11/823,481, filed on Jun. 27, 2007, now Pat. No. 7,622,559, which is a continuation of application No. 10/738,120, filed on Dec. 16, 2003, now Pat. No. 7,282,568.

(60) Provisional application No. 60/433,728, filed on Dec. 16, 2002.

(51) Int. Cl.
| | |
|---|---|
| C07K 16/24 | (2006.01) |
| A61K 39/395 | (2006.01) |
| A61K 45/06 | (2006.01) |
| C07K 16/42 | (2006.01) |
| G01N 33/68 | (2006.01) |
| A61K 39/00 | (2006.01) |

(52) U.S. Cl.
CPC ........ C07K 16/244 (2013.01); A61K 39/3955 (2013.01); A61K 45/06 (2013.01); C07K 16/4241 (2013.01); G01N 33/6869 (2013.01); A61K 2039/505 (2013.01); C07K 2317/21 (2013.01); C07K 2317/24 (2013.01); C07K 2317/31 (2013.01); C07K 2317/56 (2013.01); C07K 2317/565 (2013.01); C07K 2317/622 (2013.01); C07K 2317/92 (2013.01)

(58) Field of Classification Search
None
See application file for complete search history.

(56) References Cited

U.S. PATENT DOCUMENTS

| | | | |
|---|---|---|---|
| 5,175,384 A | 12/1992 | Krimpenfort et al. |
| 5,204,244 A | 4/1993 | Fell et al. |
| 5,306,627 A | 4/1994 | Yamada et al. |
| 5,401,643 A | 3/1995 | Yamada et al. |
| 5,434,340 A | 7/1995 | Krimpenfort et al. |
| 5,440,021 A | 8/1995 | Chuntharapai et al. |
| 5,543,503 A | 8/1996 | Chuntharapai et al. |
| 5,552,284 A | 9/1996 | Lee et al. |
| 5,571,702 A | 11/1996 | Lee et al. |
| 5,633,141 A | 5/1997 | Lee et al. |
| 5,652,338 A | 7/1997 | Matsushima et al. |
| 5,677,426 A | 10/1997 | Fong et al. |
| 5,686,070 A | 11/1997 | Doerschuk et al. |
| 5,698,196 A | 12/1997 | Matsushima et al. |
| 5,702,946 A | 12/1997 | Doerschuk et al. |
| 5,707,621 A | 1/1998 | Matsushima et al. |
| 5,707,622 A | 1/1998 | Fong et al. |
| 5,767,063 A | 6/1998 | Lee et al. |
| 5,769,269 A | 6/1998 | Peters |

(Continued)

FOREIGN PATENT DOCUMENTS

| | | |
|---|---|---|
| EP | 0315062 B1 | 5/1989 |
| EP | 0955060 A1 | 11/1999 |

(Continued)

OTHER PUBLICATIONS

Tahara, Tohru et al., "HLA antibody responses in HLA class I transgenic mice," Immunogenetics, vol. 32:351-360 (1990).

(Continued)

Primary Examiner — Yunsoo Kim
(74) Attorney, Agent, or Firm — Nelson Mullins Riley & Scarborough LLP; Jane E. Remillard, Esq.; Jeanne M. DeGiorgio, Esq.

(57) ABSTRACT

Isolated human monoclonal antibodies which bind to IL-8 (e.g., human IL-8) are disclosed. The human antibodies can be produced in a hybridoma, transfectoma or in a non-human transgenic animal, e.g., a transgenic mouse, capable of producing multiple isotypes of human monoclonal antibodies by undergoing V-D-J recombination and isotype switching. Also disclosed are pharmaceutical compositions comprising the human antibodies, non-human transgenic animals, hybridomas, and transfectomas which produce the human antibodies, and therapeutic and diagnostic methods for using the human antibodies.

15 Claims, 14 Drawing Sheets

Specification includes a Sequence Listing.

(56) References Cited

U.S. PATENT DOCUMENTS

| | | | |
|---|---|---|---|
| 5,776,457 A | 7/1998 | Lee et al. |
| 5,783,415 A | 7/1998 | Lee et al. |
| 5,831,032 A | 11/1998 | Schraufstatter et al. |
| 5,840,856 A | 11/1998 | Chuntharapai et al. |
| 5,856,457 A | 1/1999 | Lee et al. |
| 5,874,080 A | 2/1999 | Hebert et al. |
| 5,874,543 A | 2/1999 | Chuntharapai et al. |
| 5,892,017 A | 4/1999 | Lee et al. |
| 5,919,896 A | 7/1999 | Lee et al. |
| 5,922,541 A | 7/1999 | Lee et al. |
| 5,925,352 A | 7/1999 | Matsushima et al. |
| 5,939,598 A | 8/1999 | Kucherlapati et al. |
| 6,015,557 A | 1/2000 | Tobinick et al. |
| 6,075,181 A | 6/2000 | Kucherlapati et al. |
| 6,087,475 A | 7/2000 | Lee et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,177,077 B1 | 1/2001 | Tobinick |
| 6,300,129 B1 | 10/2001 | Lonberg et al. |
| 6,376,659 B1 | 4/2002 | Matsushima et al. |
| 6,379,660 B1 | 4/2002 | Saavedra et al. |
| 6,419,934 B1 | 7/2002 | Tobinick |
| 6,419,944 B2 | 7/2002 | Tobinick |
| 6,423,321 B2 | 7/2002 | Tobinick |
| 6,428,787 B1 | 8/2002 | Tobinick |
| 6,436,390 B1 | 8/2002 | Tekamp-Olson et al. |
| 6,680,209 B1 | 1/2004 | Buechler et al. |
| 6,682,736 B1 | 1/2004 | Hanson et al. |
| 6,984,720 B1 | 1/2006 | Korman et al. |
| 7,282,568 B2 | 10/2007 | Teeling et al. |
| 7,622,559 B2 | 11/2009 | Teeling et al. |
| 8,105,588 B2 | 1/2012 | Teeling et al. |
| 8,603,469 B2 | 12/2013 | Teeling et al. |
| 2001/0006637 A1 | 7/2001 | Akahoshi et al. |
| 2002/0006405 A1 | 1/2002 | Kitajima et al. |
| 2004/0208873 A1 | 10/2004 | Teeling et al. |
| 2008/0118517 A1 | 5/2008 | Teeling et al. |
| 2010/0303823 A1 | 12/2010 | Teeling et al. |
| 2012/0164143 A1 | 6/2012 | Teeling et al. |
| 2014/0170156 A1 | 6/2014 | Teeling et al. |

FOREIGN PATENT DOCUMENTS

| | | | |
|---|---|---|---|
| EP | 0966971 A1 | 12/1999 |
| EP | 0991423 B1 | 4/2000 |
| WO | 89/08665 A1 | 9/1989 |
| WO | 89/10962 A1 | 11/1989 |
| WO | 90/02178 A1 | 3/1990 |
| WO | 90/04036 A1 | 4/1990 |
| WO | 90/12878 A1 | 11/1990 |
| WO | 91/00906 A1 | 1/1991 |
| WO | 91/10741 A1 | 7/1991 |
| WO | 92/03918 A1 | 3/1992 |
| WO | 92/04372 A1 | 3/1992 |
| WO | 92/17497 A1 | 10/1992 |
| WO | 94/02602 A1 | 2/1994 |
| WO | 94/25585 A1 | 11/1994 |
| WO | 94/28931 A1 | 12/1994 |
| WO | 95/23865 A1 | 9/1995 |
| WO | 96/02576 A1 | 2/1996 |
| WO | 96/22785 A1 | 8/1996 |
| WO | 96/33735 A1 | 10/1996 |
| WO | 97/01354 A1 | 1/1997 |
| WO | 97/13852 A1 | 4/1997 |
| WO | 97/39772 A1 | 10/1997 |
| WO | 97/39775 A1 | 10/1997 |
| WO | 97/49426 A1 | 12/1997 |
| WO | 98/17312 A1 | 4/1998 |
| WO | 98/24884 A1 | 6/1998 |
| WO | 98/58671 A1 | 12/1998 |
| WO | 00/50079 A1 | 8/2000 |
| WO | 00/57902 A1 | 10/2000 |
| WO | 01/25492 A1 | 4/2001 |
| WO | 01/32879 A2 | 5/2001 |
| WO | 01/40306 A1 | 6/2001 |
| WO | 01/49321 A1 | 7/2001 |
| WO | 01/57056 A1 | 8/2001 |
| WO | 02/24217 A1 | 3/2002 |

OTHER PUBLICATIONS

Taki, Shinsuke et al., "Targeted Insertion of a Variable Region Gene into the Immunoglobulin Heavy Chain Locus," Science, vol. 262:1268-1271 (1993).

Tanaka, Toshio et al., "An Antisense Oligonucleotide Complementary to a Sequence in Ig2b Increases g2b Germline Transcripts, Stimulates B Cell DNA Synthesis, and Inhibits Immunoglobulin Secretion," The Journal of Experimental Medicine, vol. 175:597-607 (1992).

Taussig, Michael J. et al., "Regulation of immunoglobulin gene rearrangement and expression," Immunology Today, vol. 10(5):143-146 (1989).

Taylor, Lisa D. et al., "Human immunoglobulin transgenes undergo rearrangement, somatic mutation and class switching in mice that lack endogenous IgM," International Immunology, vol. 6(4):579-591 (1994).

Thomas, Kirk R. et al., "High Frequency Targeting of Genes to Specific Sites in the Mammalian Genome," Cell, vol. 44:419-428 (1986).

Thomas, Kirk R. et al., "Site-Directed Mutagenesis by Gene Targeting in Mouse Embryo-Derived Stem Cells," Cell, vol. 51:503-512 (1987).

Tomlinson, Ian M. et al., "The Repertoire of Human Germline VH Sequences Reveals about Fifty Groups of VH Segements with Different Hypervariable Loops," J. Mol. Biol., vol. 22:776-798 (1992).

Uhlmann, Eugen et al., "Antisense Oligonucleotides: A New Therapeutic Principle," Chemical Reviews, vol. 90 (4):544-584 (1990).

Vlasov, V.V. et al., "Arrest of immunoglobulin G mRNA translation in vitro with an alkylating antisense oligonucleotide derivative," Chemical Abstracts, vol. 112:28 (1990).

Weaver, David et al., "A Transgenic Immunoglobulin Mu Gene Prevents—Rearrangement of Endogenous Genes," Cell, vol. 42:117-127 (1985).

Weiss, Rick, "Mice Making Human-Like Antibodies: Medical Implications Called Stupendous," The Washington Post, Apr. 28, 1994.

Wofsy, David et al., "Reversal of Advanced Murine Lupus in ZNB/NZW F1 Mice by Treatment with Monoclonal Antibody to L3T4," The Journal of Immunology, vol. 138(10):3247-3253 (1987).

Yamamura, Ken-Ichi et al., "Cell-type-specific and regulated expression of a human g1 heavy-chain immunoglobulin gene in transgenic mice," Proc. Natl. Acad. Sci. USA, vol. 83:2152-2156 (1986).

Yancopoulos, George D. et al., "Developmentally Controlled and Tissue-Specific Expression of Unrearranged VH Gene Segments," Cell, vol. 40:271-281 (1985).

Yancopoulos, George D. et al., "Regulation of the Assembly and Expression of Variable-Region Genes," Annual Reviews, vol. 4:339-368 (1986).

Yang, Xiao-Dong et al., "Fully human anti-interleukin-8 monoclonal antibodies: potential therapeutics for the treatmeni of inflammatory disease states," Journal of Leukocyte Biology, vol. 66:401-410 (1999).

Yasui, Hisashi et al., "Class switch from m to d is mediated by homologous recombination between sm and Sm sequences in human immunoglobulin gene loci," Eur. J. Immunol., vol. 19:1399-1403 (1989).

Zijlstra, Maarten et al., "Germ-line transmission of a disrupted b2-microglobulin gene produced by homologous recombination ni embryonic stem cells," Nature, vol. 342:435-438 (1989).

Zimmer, Andreas et al., "Production of chimaeric mice containing embryonic stem (ES) cells carrying a homoeobox Hox 1.1 allele mutated by homologous recombination," Nature, vol. 338:150-153 (1989).

(56) References Cited

OTHER PUBLICATIONS

U.S. Appl. No. 14/074,226, filed Nov. 7, 2013, Jessica Teeling.
U.S. Appl. No. 13/337,798, filed Dec. 27, 2011, Jessica Teeling.
U.S. Appl. No. 12/616,615, filed Nov. 11, 2009, Jessica Teeling.
U.S. Appl. No. 11/823,481, filed Jun. 27, 2007, Jessica Teeling.
U.S. Appl. No. 10/738,120, filed Dec. 16, 2003, Jessica Teeling.
U.S. Appl. No. 14/074,226, Nov. 10, 2014.
U.S. Appl. No. 14/074,226, Aug. 14, 2015.
U.S. Appl. No. 13/337,798, Aug. 9, 2013.
U.S. Appl. No. 13/337,798, Dec. 28, 2013.
U.S. Appl. No. 13/337,798, Jul. 30, 2012.
U.S. Appl. No. 12/616,615, Sep. 20, 2011.
U.S. Appl. No. 12/616,615, Mar. 24, 2011.
U.S. Appl. No. 12/616,615, Oct. 20, 2010.
U.S. Appl. No. 11/823,481, Jul. 17, 2009.
U.S. Appl. No. 11/823,481, Feb. 11, 2009.
U.S. Appl. No. 10/738,120, Apr. 27, 2007.
U.S. Appl. No. 10/738,120, Sep. 11, 2006.
U.S. Appl. No. 10/738,120, Dec. 15, 2005.
U.S. Appl. No. 10/738,120, Aug. 8, 2005.
Alt, Frederick W. et al., "Immunoglobulin genes in transgenic mice," TIG, vol. 1:231-236 (1985).
Attwood, Teresa K., "The Babel of Bioinformatics," Science, vol. 290:471-473 (2000).
Berman, Jeffrey E. et al., "Content and organization of the human Ig VH locus: definition of three new VH families and linkage to the Ig CH locus," The EMBO Journal, vol. 7(3):727-738 (1988).
Berton, Michael T. et al., "Synthesis of germ-line g1 immunoglobulin heavy-chain transcripts in resting B cells: Induction by interleukin 4 and inhibition by interferon g," Proc. Natl. Acad. Sci. USA, vol. 86:2829-2833 (1989).
Bollag, Roni J. et al., "Homologous Recombination in Mammalian Cells," Annu. Rev. Genet., vol. 23:199-225 (1989).
Brüggemann, Marianne et al., "A repertoire of monoclonal antibodies with human heavy chains from transgenic mice," Proc. Natl. Acad. Sci. USA, vol. 86:6709-6713 (1989).
Brüggemann, Marianne et al., "Human antibody production in transgenic mice: expression from 100 kb of the human IgH locus," Eur. J. Immunol., vol. 21:1323-1326 (1991).
Bucchini, D. et al., "Rearrangement of a chicken immunoglobulin gene occurs in the lymphoid lineage of transgenic mice," Nature, vol. 326:409-411 (1987).
Buttin, G., "Exogenous Ig gene rearrangement in transgenic mice: a new strategy for human monoclonal antibody production?" TIG, vol. 3(8):205-206 (1987).
Capecchi, Mario R., "Altering the Genome by Homologous Recombination," Science, vol. 244:1288-1292 (1989).
Capecchi, Mario R., "The New Mouse Genetics: Altering the Genome by Gene Targeting," TIG, vol. 5(3):70-76 (1989).
Chen, Pojen P. et al., "Characterization of Two Immunoglobulin VH Genes that are Homologous to Human Rheumatoid Factors," Arthritis and Rheumatism, vol. 32(1):72-76 (1989).
Coffman, Robert L. et al., "A Mouse T Cell Product that Preferentially Enhances IgA Production, I. Biologic Characterization," The Journal of Immunology, vol. 139(11):3685-3690 (1987).
Coffman, Robert L. et al., "A T Cell Activity that Enhances Polyclonal IgE Production and its Inhibition by Interferon-g," The Journal of Immunology, vol. 136(3):949-954 (1986).
Doetschman, Thomas et al., "Targetted correction of a mutant HPRT gene in mouse embryonic stem cells," Nature, vol. 330:576-578 (1987).
Durdik, Jeannine et al., "Isotype switching by a microinjected m immunoglobulin heavy chain gene in transgenic mice," Proc. Natl. Acad. Sci. USA, vol. 86:2346-2350 (1989).
Esser, Charlotte et al., "Rapid induction of transcription of unrearranged sg1 switch regions in activated murine B cells by interleukin 4," The EMBO Journal, vol. 8(2):483-488 (1989).
Ferrier, Pierre et al., "Separate elements control DJ and VDJ rearrangement in a transgenic recombination substrate," The EMBO Journal, vol. 9(1):117-125 (1990).

Fishwild, Dianne M. et al., "High-avidity human IgGk monoclonal antibodies from a novel strain of minilocus transgenic mice," Nature Biotechnology, vol. 14(7):845-851 (1996).
Forni, Luciana et al., "Extensive splenic B cell activation in IgM-transgenic mice," Eur. J. Immunol., vol. 20:983-989 (1990).
Gerstein, Rachel M. et al., "Isotype Switching of an Immunoglobulin Heavy Chain Transgene Occurs by DNA Recombination between Different Chromosomes," Cell, vol. 63:537-548 (1990).
Goodhardt, M. et al., "Rearrangement and expression of rabbit immunoglobulin k light chain gene in transgenic mice," Proc. Natl. Acad. Sci. USA, vol. 84:4229-4233 (1987).
Gordon, Jon W., "Transgenic Mice in Immunology," The Mount Sinai Journal of Medicine, vol. 53(3):223-231 (1986).
Green, L.L. et al., "Antigen-specific human monoclonal antibodies from mice engineered with human Ig heavy and light chain YACs," Nature Genetics, vol. 7:13-21 (1994).
Hagman, James et al., "Inhibition of Immunoglobulin Gene Rearragement by the Expression of a l2 Transgene," J. Exp. Med., vol. 169:1911-1929 (1989).
Hofker, Marten H. et al., "Complete physical map of the human immunoglobulin heavy chain constant region gene complex," Proc. Natl. Acad. Sci. USA, vol. 86:5567-5571 (1989).
Huang, Suyun et al., "Fully Humanized Neutralizing Antibodies to Interleukin-8 (ABX-IL8) Inhibit Angiogenesis, Tumor Growth, and Metastasis of Human Melanoma," American Journal of Pathology, vol. 161(1):125-134 (2002).
Humphries, C.G. et al., "A new human immunoglobulin VH family preferentially rearranged in immature B-cell tumours," Nature, vol. 331:446-449 (1988).
Ichihara, Y. et al., "Organization of human immunoglobulin heavy chain diversity gene loci," The EMBO Journal, vol. 7(13):4141-4150 (1988).
Iglesias, Antonio et al., "Expression of immunoglobulin delta chain causes allelic exclusion in transgenic mice," Nature, vol. 330:482-484 (1987).
Jaenisch, Rudolf, "Transgenic Animals," Science, vol. 240:1468-1474 (1988).
Jakobovits, Aya et al., "Analysis of homozygous mutant chimeric mice: Deletion of the immunoglobulin heavy-chain joining region blocks B-cell development and antibody production," Proc. Natl. Acad. Sci. USA, vol. 90:2551-2555 (1993).
James, Keith et al., "Human monoclonal antibody production, Current status and future prospects," Journal of Immunological Methods, vol. 100:5-40 (1987).
Janeway, Charles A. Jr., Immunobiology, Third Edition, pp. 3:7-3:11 (1997).
Jasin, Maria et al., "Homologous integration in mammalian cells without target gene selection," Genes & Development, vol. 2:1353-1363 (1988).
Ji, Yong-yong et al., "Flow Cytometry Analysis of the Neutralization Effect of Anti-iL-8 MCABS on IL-8-Activated Human Granulocytes," Shi yan sheng wu xue bao, vol. 28(3):257-261 (1995).
Jonker, M. et al., "In vivo treatment with a monoclonal chimeric anti-CD4 antibody results in prolonged depletion of circulating CD4+ cells in chimpanzees," Clin. Exp. Immunol., vol. 93:301-307 (1993).
Jung, Steffen et al., "Shutdown of Class Switch Recombination by Deletion of a Switch Region Control Element," Science, vol. 259:984-987 (1993).
Kenny, James J. et al., "Alteration of the B Cell Surface Phenotype, Immune Response to Phosphocholine and the B Cell Repertoire in M167 m Plus k Transgenic Mice," The Journal of Immunology, vol. 142(12):4466-4474 (1989).
Kitamura, Dalsuke et al., "A B cell-deficient mouse by targeted disruption of the membrane exon of the immunoglobulin m chain gene," Nature, vol. 350:423-426 (1991).
Knox, Susan J. et al., "Observation on the Effect of Chimeric Anti-CD4 Monoclonal Antibody in Patients With Mycosis Fungoides," Blood, vol. 77(1):20-30 (1991).
Koller, Beverly H. et al., "Inactivating the b2-microglobulin locus in mouse embryonic stem cells in homologous recombination," Proc. Natl. Acad. Sci. USA, vol. 86:8932-8935 (1989).

(56) References Cited

OTHER PUBLICATIONS

Kurdowska, A. et al., "An Anti-Interleukin 8 Monoclonal Antibody That Interferes with the Binding of Interleukin 8 to Cellular Receptors and the Activation of Human Blood Neutrophils," Hybridoma, vol. 14(3):225-233 (1995).
Lin, F.-L. et al., "Recombination in mouse L cells between DNA introduced into cells and homologous chromosomal sequences," Proc. Natl. Acad. Sci. USA, vol. 82:1391-1395 (1985).
Linton, Phyllis-Jean et al., "Primary Antibody-Forming Cells and Secondary B Cells Are Generated from Separate Precursor Cell Subpopulations," Cell, vol. 59:1049-1059 (1989).
Lo, David et al., "Expression of mouse IgA by transgenic mice, pigs and sheep," Eur. J. Immunol., vol. 21:1001-1006 (1991).
Lonberg, Nils et al., "Antigen-specific human antibodies from mice comprising four distinct genetic modifications," Nature, vol. 368:856-859 (1994).
Lorenz, Wulfing et al., "Physical map of the human immunoglobulin K locus and its implications for the mechanism of VK-JK rearrangement," Nucleic Acids Research, vol. 15(23):9667-9676 (1987).
Lutzker, Stuart et al., "Structure and Expression of Germ Line Immunoglobulin g2b Transcripts," Molecular and Cellular Biology, vol. 8(4):1849-1852 (1988).
Mansour, Suzanne L. et al., "Disruption of the proto-oncogene int-2 in mouse embryo-derived stem cells: a general strategy for targeting mutations to non-selectable genes," Nature, vol. 336:348-352 (1988).
Sedivy, John M. et al., "Positive genetic selection for gene disruption in mammalian cells by homologous recombination," Proc. Natl. Acad. Sci. USA, vol. 86:227-231 (1989).
Sekido, Nobuaki et al., "Prevention of lung reperfusion injury in rabbits by a monoclonal antibody against interleukin-8," Nature, vol. 365:654-657 (1993).
Shimizu, Akira et al., "Immunoglobulin double-isotype expression by trans-mRNA in a human immunoglobulin transgenic mouse," Proc. Natl. Acad. Sci. USA, vol. 86:8020-8023 (1989).
Shimizu, Akira et al., "Trans-Splicing as a Possible Molecular Mechanism for the Multiple Isotype Expression of the Immunoglobulin Gene," J. Exp. Med., vol. 173:1385-1393 (1991).
Sideras, Paschalis et al., "Production of sterile transcripts of Cg genes in an IgM-producing human neoplastic B cell line that switches to IgG-producing cells," International Immunology, vol. 1(6):631-642 (1989).
Siebenlist, U. et al., "Human immunoglobulin D segments encoded in tandem multigenic families," Nature, vol. 294:631-635 (1981).
Skolnick, Jeffrey et al., "From genes to protein structure and function: novel applications of computational approaches in the genomic era," Trends Biotechnol., vol. 18(1):34-39 (2000).
Smithies, Oliver et al., "Insertion of DNA sequences into the human chromosomal b-globin locus by homologous recombination," Nature, vol. 317:230-234 (1985).
Snapper, Clifford M. et al., "Interferon-g and B Cell Stimulatory Factor-1 Reciprocally Regulate Ig Isotype Production," Science, vol. 236:944-947 (1987).
Song, Kyu-Young et al., "Accurate modification of a chromosomal plasmid by homologous recombination in human cells," Proc. Natl. Acad. Sci. USA, vol. 84:6820-6824 (1987).
Soriano, Philippe et al., "Targeted Disruption of the c-src Proto-Oncogene Leads to Osteopetrosis in Mice," Cell, vol. 64:693-702 (1991).
Stavnezer, Janet et al., "Immunoglobulin heavy-chain switching may be directed by prior induction of transcripts from constant-region genes," Proc. Natl. Acad. Sci. USA, vol. 85:7704-7708 (1988).
Stites, Daniel P. et al., "Immunoglobulins II: Gene Organization & Assembly," Basic & Clinical Immunology, Chpt. 5, p. 50 (1984).
Storb, Ursula et al., "Expression, Allelic Exclusion and Somatic Mutation of Mouse Immunoglobulin Kappa Genes," Immunological Reviews, vol. 89:85-102 (1986).
Storb, Ursula, "Immunoglobulin Gene Analysis in Transgenic Mice," Immunoglobulin Genes, Chpt. 16, pp. 303-326 (1989).
Supplementary European Search Report for Application No. EP03799925, 2 pages, dated Sep. 25, 2008.
Szurek, Paul et al., "Complete Nucleotide Sequence of the Murine g3 Switch Region and Analysis of Switch Recombination Sites in Two g3-Expressing Hybridomas," The Journal of Immunology, vol. 135(1):620-626 (1985).
Metzler, W.J. et al., "Solution structure of human CTLA-4 and delination of the CD80/CD86 binding site conserved in CD28," Nature Structural Biology, vol. 4(7):527-531 (1997).
Miller, Jim et al., "Structural alterations in J regions of mouse immunoglobulin I genes are associated with differential gene expression," Nature, vol. 295:428-430 (1982).
Mills, Frederick C. et al., "DNase I hypersensitive sites in the chromatin of human m immunoglobulin heavy-chain genes," Nature, vol. 306:809-812 (1983).
Mills, Frederick C. et al., "Sequences of human immunoglobulin switch regions: implications for recombination and transcription," Nucleic Acid Research, vol. 18(24):7305-7316 (1990).
Morrison, Sherie L., "Success in specification," Nature, vol. 368:812-813 (1994).
Mowatt, Michael R. et al., "DNA Sequence of the Murine g1 Switch Segment Reveals Novel Structural Elements," The Journal of Immunology, vol. 136(7):2674-2683 (1986).
Murray, Andrew W. et al., "Construction of artificial chromosomes in yeast," Nature, vol. 305:189-193 (1983).
Müller, Werner et al., "Membrane-bound IgM obstructs B cell development in transgenic mice," Eur. J. Immunol., vol. 19:923-928 (1989).
Neuberger, M.S. et al., "Isotype exclusion and transgene down-regulation in immunoglobulin-I transgenic mice," Nature, vol. 338:350-352 (1989).
Neuberger, Michael, "Generating high-avidity human Mabs in mice," Nature Biotechnology, vol. 14:826 (1996).
Newman, Roland et al., "'Primatization' of Recombinant Antibodies for Immunotherapy of Human Diseases: a Macaque/Human Chimeric Antibody Against Human CD4," Biotechnology, vol. 10:1455-1460 (1992).
Nikaido, Toshio et al., "Nucleotide Sequences of Switch Regions of Immunoglobulin Ce and Cg Genes and Their comparison," The Journsl of Biological Chemistry, vol. 257(13):7322-7329 (1982).
Nikaido, Toshio et al., "Switch region of immunoglobulin Cm gene is composed of simple tandem repetitive sequences," Nature, vol. 292:845-848 (1981).
Nussenzweig, Michel C. et al., "A human immunoglobulin gene reduces the incidence of lymphomas in c-Myc-bearing transgenic mice," Nature, vol. 336:446-450 (1988).
Nussenzweig, Michel C. et al., "Allelic Exclusion in Transgenic Mice Carrying Mutant Human IgM Genes," J. Exp. Med., vol. 167:1969-1974 (1988).
Oettinger, Marjorie A. et al., "RAG-1 and RAG-2, Adjacent Genes That Synergistically Activate V(D)J Recombination," Science, vol. 248:1517-1523 (1990).
Paul, William P., Fundamental Immunology, Third Edition, p. 242 (1993).
Petters, R.M., "Transgenic Mice in Immunological Research," Veterinary Immunology and Immunopathology, vol. 17:267-278 (1987).
Pettersson, Sven et al., "A second B cell-specific enhancer 3' of the immunoglobulin heavy-chain locus," Nature, vol. 344:165-168 (1990).
Portolano, Stefano et al., "Lack of Promiscuity in Autoantigen-Specific H and L Chain Combinations as Revealed by Human H and L Chain 'Roulette'," The Journal of Immunology, vol. 150(3):880-887 (1993).
Powelson, John A. et al., "CDR-Grafted OKT4A Monoclonal Antibody in Cynomolgus Renal Allograft Recipients," Transplantation, vol. 57(6):788-793 (1994).
Rabbitts, T.H. et al., "Human immunoglobulin heavy chain genes: evolutionary comparisons of Cm, Cd and Cg genes and associated switch sequences," Nucleic Acids Research, vol. 9(18):4509-4524 (1981).

(56) References Cited

OTHER PUBLICATIONS

Rath, Satyajit et al., "B Cell Abnormalities Induced by A m Ig Transgene Extend to L Chain Isotype Usage," The Journal of Immunology, vol. 146(8):2841-2847 (1991).

Rath, Satyajit et al., "Quantitative Analysis of Idotypic Mimicry and Alelic Exclusion in Mice with A m Ig Transgene," The Journal of Immunology, vol. 143(6):2074-2080 (1989).

Ravetch, J.V. et al., "Evolutionary approach to the question of immunoglobulin heavy chain switching: Evidence from cloned human and mouse genes," Proc. Nal Acad. Sci. USA, vol. 77(11):6734-6738 (1980).

Reid, Laurence E. et al., "A single DNA response element can confer inducibility by both a- and g-interferons," Proc. Natl. Acad. Sci. USA, vol. 86:840-844 (1989).

Ritchie, Kindred A. et al., "Allelic exclusion and control of endogenous immunoglobulin gene rearrangement in k transgenic mice," Nature, vol. 312:517-520 (1984).

Rothman, Paul et al., "Structure and expression of germline immunoglobulin g3 heavy chain gene transcripts: Implications for mitogen and lymphokine directed class-switching," International Immunology, vol. 2(7):621-627 (1990).

Rudikoff, Stuart et al., "Single amino acid substitution altering antigen-binding specificity," Proc. Natl. Acad. Sci USA, vol. 79:1979-1983 (1982).

Rusconi, Sandro et al., "Transmission and expression of a specific pair of rearranged immunoglobulin m and k genes in a transgenic mouse line," Nature, vol. 314:330-334 (1985).

Salcedo, Rosalba et al., "Combined Administration of Antibodies to Human Interleukin 8 and Epidermal Growth Factor Receptor Results in Incrased Antimetastatic Effects on Human Breast Carcinoma-Xenografts," Clinical Cancer Reseasrch, vol. 8:2655-2665 (2002).

Sato, Takayuki et al., "Physical linkage of a variable region segment adn the joining region segment of the human immunoglobulin heavy chain locus," Biochemical and Biophysical Research Communications, vol. 154(1):265-271 (1988).

3CANGOS, George et al., "Gene Transfer into Mice," Advances in Genetics, vol. 24:285-322 (1987).

10F8 V_L:

<u>atggaaacccagctgcagcttcttcttcctcctgctactctggctcccagatacaccaccggagaaattgttgacgcagtctccaggcaccctgtctttgtctccaggggaaagagccaccctctcctgcagggccagtcagagtattagcagcagctactttagcctggtacca</u>
gcagaaacctggccaggctcccaggctcctcatctatggtgcatccagcagggccactggcatcccagacagattcagtggcagtgggtctgggacagacttcactctcaccatcagcagactggagcctgaagattttgcagtgtattactgtgcagagtatgcggtcta
ctcactttcggcggtgggaccaaagtggatatcaaa

10F8 V_H:

<u>atggagtttggactgagctgggttttccttgttgctattttaagaggtgtccagtgtcaggtgcaactggtggagtctgggggaggcgtggtccagcctgggaggtccctgagactctcctgtacagcgtctggattcacctttagtcactactggatgcactgggtccgccag</u>
gctccaggcaaggggctggagtgggtggcagttatcgttatgatggaagtaataaatacagcagactcccgtgaagggccgattcaccatctccagagacaattccaagaacacgttatatctgcaaatgaacagcctgagagccgaggacacggctgtgtattactgt
gcgagagataggggtggggtctttgactactttgactatgggccaggaaccctggtcaccgtctcctca Leader sequences are underlined

Fig. 1

Light (kappa) chain V regions cloned, DNA sequences

```
Vκ A-27
Germline:    GAA ATT GTG TTG ACG CAG TCT CCA GGC ACC CTG TCT TTG TCT CCA GGG GAA AGA GCC ACC CTC TCC TGC
10F8 Vκ:     --- --- --- --- --- --- --- --- --- --- --- --- --- --- --- --- --- --- --- --- --- --- ---
                                                     ──────────CDR1──────────
Germline:    AGG GCC AGT CAG AGT GTT AGC AGC TAC TTA GCC TGG TAC CAG CAG AAA CCT GGC CAG GCT CCC AGG
10F8 Vκ:     --- --- --- --- --- --- A-- --- --- --- --- --- --- --- --- --- --- --- --- --- --- ---
                                         ──────CDR2──────
Germline:    CTC CTC ATC TAT GGT GCA TCC AGC AGG GCC ACT GGC ATC CCA GAC AGG TTC AGT GGC AGT GGG TCT GGG
10F8 Vκ:     --- --- --- --- --- --- --- C-- --- --- --- --- --- --- --- --- --- --- --- --- --- ---
                                                                                                 ──CDR3
Germline:    ACA GAC TTC ACT CTC ACC ATC AGC AGA CTG GAG CCT GAA GAT TTT GCA GTG TAT TAC TGT CAG CAG TAT
10F8 Vκ:     --- --- --- --- --- --- --- --- --- --- --- --- --- --- --- --- --- --- --- --- --- --- ---
             ─────CDR3─────                          ────────Jκ3────────
Germline:    GGT AGC TCA CC
10F8 Vκ:     -C- G--  ---   -TC ACT TTC GGC CCT GGG ACC AAA GTG GAT ATC AAA C
```

Fig. 2

Light (kappa) chain V regions cloned, protein sequences

```
                                            CDR1                            CDR2
V_K A-27
Germline:   EIVLTQSPGTLSLSPGERATLSC   RASQSVSSSYLA   WYQQKPGQAPRLLIY   GASSRAT
10F8 V_K:   ----------------------    -----I------   ---------------   --P----

CDR3
Germline:   GIPDRFSGSGSGTDFTLTISRLEPEDFAVYYC   QQYGSSP    AG-LT   FGPGTKVDIK
10F8 V_K:   --------------------------------   -------    ---AG-LT  FGPGTKVDIK   (J_K3)
```

Fig. 3

Heavy chain V regions cloned, DNA sequences

```
V_H 3-33
Germline:   CAG GTG CAG CTG GTG GAG TCT GGG GGA GGC GTG GTC CAG CCT GGG AGG TCC CTG AGA CTC TCC TGT GCA GCG
10F8:       --- --- --- --A --- --- --- --- --- --- --- --- --- --- --- --- --- --- --- --- --- A-- ---

CDR1
Germline:   TCT GGA TTC ACC TTC AGT AGC TAT GGC ATG CAC TGG GTC CGC CAG GCT CCA GGC AAG GGG CTG GAG TGG GTG
10F8:       --- --- --- --- --- --- CA- --- --- T-- --- --- --- --- --- --- --- --- --- --- --- --- ---

CDR2
Germline:   GCA GTT ATA TGG TAT GAT GGA AGT AAT AAA TAC TAT GCA GAC TCC GTG AAG GGC CGA TTC ACC ATC TCC AGA
10F8:       --- --- --- --- --- --- --- --- T-- G-- --- --- A-- --- --- --- --- --- --- --G --- --- --- ---

Germline:   GAC AAT TCC AAG AAC ACG CTG TAT CTG CAA ATG AAC AGC CTG AGA GCC GAG GAC ACG GCT GTG TAT TAC TGT
10F8:       --- --- --- --- --- --- --- --- --- --- --- --- --- --- --- --- --- --- --- --- --- --- ---

CDR3
                    n-D-n           J_H 4 (b)
Germline:   GCG AGA GA                    TAC TTT GAC TAC TGG GGC CAG GGA ACC CTG GTC ACC GTC TCC TCA G
10F8:       --- --- --T AGG GTG GGG CT-   --- --- --- --T --- --- --- --- --- --- --- --- --- --- --- -
```

*Fig. 4*

Heavy chain V region cloned, protein sequence

```
                                    _CDR1_                        _CDR2_
                                    SYGMH   WVRQAPGKGLEWVA        VIWYDGSNKYYADSVKG
V_H 3-33
Germline:  QVQLVESGGGVVQPGRSLRLSCAASGFTFS
10F8:      ------------------------T-----  H---Y   --------------        ------YE-N-------

_CDR3_
Germline:  RFTISRDNSKNTLYLQMNSLRAEDTAVYYCAR        DRVGLFDY   WGQGTLVTVSS    (J_H4[b])
10F8:      -------------------------------         --------   -----------
```

Fig. 5

HUMAN MONOCLONAL ANTIBODIES AGAINST INTERLEUKIN 8 (IL-8)

RELATED APPLICATIONS

This application is a continuation of U.S. patent application Ser. No. 14/074,226, filed on Nov. 7, 2013, which is a divisional of U.S. patent application Ser. No. 13/337,798, filed on Dec. 27, 2011, which is a divisional of U.S. patent application Ser. No. 12/616,615, filed on Nov. 11, 2009, which is a continuation of U.S. patent application Ser. No. 11/823,481, filed on Jun. 27, 2007, which is a continuation of U.S. patent application Ser. No. 10/738,120, filed Dec. 16, 2003, which claims the benefit of U.S. Provisional Patent Application Ser. No. 60/433,728, filed Dec. 16, 2002, the entire contents of which are incorporated herein by this reference.

SEQUENCE LISTING

The instant application contains a Sequence Listing which has been submitted in ASCII format via EFS-Web and is hereby incorporated by reference in its entirety. Said ASCII copy, created on Jun. 15, 2016, is named GMI-278CN2DV2CN_Sequence Listing.txt and is 18,507 bytes in size.

BACKGROUND OF THE INVENTION

Chemokines represent a superfamily of about 30 chemotactic cytokines acting as vital initiators and promulgators of inflammatory reactions. They range from 8 to 11 kD in molecular weight, are active over a 1 to 100 ng/mL concentration range, and are produced by a wide variety of cell types.

Interleukin 8 (IL-8), formerly called monocyte-derived neutrophil chemotactic factor (MDNCF) or neutrophil attractant/activation protein-1 (NAP-1), is a chemokine and a member of the cytokine family that displays chemotactic activity for specific types of leukocytes. IL-8 is a member of the CXC chemokine family in which an amino acid is present between the first two of four highly conserved cysteine residues. IL-8 is a polypeptide of which two predominant forms consist of 72 amino acids and 77 amino acids. Monocytes, macrophages, neutrophils, lymphocytes, dermal fibroblasts, keratinocytes, vascular endothelial cells, melanocytes, hepatocytes, and various tumor cell lines produce IL-8. IL-8 is a potent neutrophil chemokine and participates in the migration of neutrophils towards inflammatory sites. Upon binding to its high-affinity receptors (CXCR1 and CXCR2) which are present on the surface of neutrophils, IL-8 activates neutrophils by accelerating degranulation and elevating the free $Ca^{2+}$ concentration in the cytoplasm and also induces neutrophil migration to thereby destroy the infiltrated tissue.

Although the neutrophil inflammatory response is essential for the destruction of bacteria which are invading the body, inappropriate neutrophil activation can cause a number of inflammatory disorders. For example, IL-8 has been recovered from inflammatory sites such as, pustulosis palmoplantaris (PPP) lesions, psoriatic scales, synovial fluid of patients with rheumatoid arthritis (RA), pleural fluid from empyema patients, alveolar macrophages from lungs with idiopathic pulmonary fibrosis, broncheoalveolar lavage fluids from patients with adult respiratory distress syndrome, cystic fibrosis, chronic bronchitis, and bronchiectasis. IL-8 is also associated with sepsis, asthma, glomerulonephritis, inflammatory bowel disease (IBD), ischaemia-reperfusion injury and multiple myeloma. Such conditions are characterized by inflammation accompanied by neutrophil infiltration and tissue damage.

IL-8 is also known to promote angiogenesis and, thus, growth of tumors. Such activity has been associated with the ELR motif within the IL-8 sequence. Human tumor cell lines such as, thyroid carcinoma, transitional cell carcinoma, trichilemmona, squamous cell carcinoma, and melanoma constitutively express IL-8 which plays a role in tumor invasion and metastasis.

Accordingly, antibodies specific for IL-8 are therapeutically important for treating diseases mediated by IL-8 activity. A hybridoma producing a human antibody against human IL-8, referred to as 2C6, has been described previously (U.S. Pat. No. 6,300,129 by Lonberg and Kay). However, additional antibodies specific for IL-8 are still needed.

SUMMARY OF THE INVENTION

The present invention provides isolated human monoclonal antibodies which bind to human IL-8, as well as bispecific and multispecific molecules and other therapeutic compositions containing such antibodies, alone or in combination with additional therapeutic agents. Also provided are methods for treating a variety IL-8 mediated diseases using the antibodies and compositions of the invention.

The fully human antibodies of the present invention bind to IL-8 and inhibit IL-8 function (and IL-8 mediated effects) by blocking IL-8 binding to its receptor. For example, the antibodies can inhibit proinflammatory and angiogenic effects induced by IL-8, such as IL-8 induced chemotactic activity for leukocytes and IL-8 induced calcium flux. The antibodies can also inhibit IL-8 induced increased expression of CD11b (Mac-1) and decreased expression of L-selectin (CD62L). Accordingly, particular antibodies of the invention have one or more of the following characteristics:

(i) inhibits IL-8 binding to its receptors (CXCR1 and CXCR2);

(ii) inhibits IL-8 induced proinflammatory effects;

(iii) inhibits IL-8 induced chemotactic activity for neutrophils;

(iv) inhibits IL-8 induced calcium flux;

(v) inhibits IL-8 induced changes in expression levels of adhesion molecules on neutrophils;

(vi) inhibits IL-8 induced increased expression of CD11b (Mac-1) and inhibits IL-8 induced decreased expression of L-selectin on neutrophils;

(vii) does not cross-react with related chemokines selected from the group consisting of human GRO-α, human GRO-β, human IP-10 and human NAP-2;

(viii) significantly inhibits chemotaxis induced by biological fluids which contain multiple chemotactic factors including IL-8.

Therefore, the human antibodies of the present invention provide an improved means for treating and preventing disorders mediated by IL-8 activity attributable in part to their unique specificity (e.g., epitope specificity and lack of cross-reactivity with related chemokines), affinity, structure, functional activity and the fact that they are fully human, making them significantly less immunogenic and more therapeutically effective and useful when administered to human patients than other IL-8 antibodies previously generated (e.g., murine and humanized antibodies).

Isolated human antibodies of the invention include a variety of antibody isotypes, such as IgG1, IgG2, IgG3, IgG4, IgM, IgA1, IgA2, secretory IgA, IgD, and IgE. Typically, they include IgG1 (e.g., IgG1,κ or IgG1,λ), IgG3, IgG4 and IgM isotypes. The antibodies can be intact (e.g., an IgG1 or IgG3 antibody) or can include only an antigen-binding portion (e.g., a Fab, F(ab')$_2$, Fv or a single chain Fv fragment).

Particular therapeutic antibodies of the invention include human monoclonal antibody (HuMab) 10F8 and functionally equivalent antibodies which (a) are encoded by human heavy chain and human light chain nucleic acids comprising nucleotide sequences in their variable regions as set forth in SEQ ID NO:10 and SEQ ID NO:6, respectively, and sequences which are at least 95% homologous therewith, or (b) include heavy chain and light chain variable regions which comprise the amino acid sequences shown in SEQ ID NO:12 and SEQ ID NO:8, respectively, and sequences which are at least 95% homologous therewith.

Still other particular human antibodies of the invention include those which comprise a CDR domain having a human heavy and light chain CDR1 region, a human heavy and light chain CDR2 region, and a human heavy and light chain CDR3 region, wherein the antibody comprises at least one CDR sequence selected from the group consisting of: $V_L$ CDR1 of SEQ ID NO: 16, $V_L$ CDR2 of SEQ ID NO: 17, $V_L$ CDR3 of SEQ ID NO: 18, $V_H$ CDR1 of SEQ ID NO: 22, $V_H$ CDR2 of SEQ ID NO: 23, and $V_H$ of SEQ ID NO: 24. Antibodies which comprise at least the $V_H$ CDR3 of SEQ ID NO: 24 are also encompassed by the present invention, as well as antibodies which comprise at least four CDR sequences selected from the group consisting of: $V_L$ CDR1 of SEQ ID NO: 16, $V_L$ CDR2 of SEQ ID NO: 17, $V_L$ CDR3 of SEQ ID NO: 18, $V_H$ CDR1 of SEQ ID NO: 22, $V_H$ CDR2 of SEQ ID NO: 23, and $V_H$ of SEQ ID NO: 24 and antibodies which comprise the six CDR sequences: $V_L$ CDR1 of SEQ ID NO: 16, $V_L$ CDR2 of SEQ ID NO: 17, $V_L$ CDR3 of SEQ ID NO: 18, $V_H$ CDR1 of SEQ ID NO: 22, $V_H$ CDR2 of SEQ ID NO: 23, and $V_H$ of SEQ ID NO: 24.

The present invention further includes antibodies which bind to an epitope on human IL-8 defined by antibody 10F8, and/or which compete for binding to IL-8 with antibody 10F8, or which have other functional binding characteristic exhibited by antibody 10F8. Such antibodies include those which bind to IL-8 with a dissociation equilibrium constant ($K_D$) of approximately $10^{-8}$M or less, $10^{-9}$ M or less, $10^{-10}$ M or less, or $10^{-11}$ M or even less. Such antibodies also include those which do not cross-react with related chemokines, e.g., human GRO-α, human GRO-β, IP-10 or human NAP-2, and thus do not inhibit their function.

In another aspect, human antibodies of the invention can be co-administered with one or more further therapeutic agents. They can be coadministered simultaneously with such agents (e.g., in a single composition or separately) or can be administered before or after administration of such agents. Such further agents can include agents for treating inflammatory or hyperproliferative skin disorders, immunosuppressive agents, anti-inflammatory agents, or chemotherapeutic agents.

In another aspect, the present invention provides compositions, e.g., pharmaceutical or diagnostic compositions, comprising one or more (i.e., a combination of) human anti-IL-8 antibodies together with a pharmaceutically acceptable carrier. The composition can further include one or more other therapeutic agents, such as those disclosed above.

For use in in vivo treatment and prevention of IL-8 mediated diseases, human antibodies of the present invention are administered to patients (e.g., human subjects) at therapeutically effective dosages using any suitable route of administration, such as injection or infusion and other routes of administration known in the art for antibody-based clinical products.

In yet another aspect, the invention provides methods for inhibiting the proinflammatory effects of IL-8, such as IL-8 induced chemotactic activity for leukocytes.

Accordingly, human antibodies of the present invention can be used to treat and/or prevent a variety of IL-8 mediated diseases by administering the antibodies to patients suffering from such diseases.

Exemplary diseases that can be treated (e.g., ameliorated) or prevented using the methods and compositions of the invention include, but are not limited to, inflammatory or hyperproliferative skin disorders, immune, autoimmune, inflammatory or infectious diseases, and diseases involving IL-8 mediated angiogenesis, such as tumors and cancers.

In yet another aspect, the present invention provides a method for detecting in vitro or in vivo the presence of IL-8 in a sample or an individual, e.g., for diagnosing an IL-8-related disease. This can also be useful for monitoring a IL-8 related disease and the effect of treatment with an anti-IL-8 antibody and for determining and adjusting the dose of the antibody to be administered. In one embodiment, the presence of IL-8 is detected by contacting a sample to be tested, optionally along with a control sample, with a human monoclonal antibody of the invention under conditions that allow for formation of a complex between the antibody and IL-8. Complex formation is then detected (e.g., using an ELISA). When using a control sample along with the test sample, complex is detected in both samples and any statistically significant difference in the formation of complexes between the samples is indicative of the presence of IL-8 in the test sample.

In a further aspect, the invention relates to anti-idiotypic antibodies which bind to the human monoclonal antibodies of the invention. These anti-idiotypic antibodies can be used as an immunodiagnostic tool to detect and quantify levels of human monoclonal antibodies against IL-8 in laboratory or patient samples. This may be useful for examining pharmacokinetics of the anti-IL-8 antibody or for determining and adjusting the dosage of the anti-IL-8 antibody and for monitoring the disease and the effect of treatment in a patient.

Mouse anti-idiotypic antibodies can be made, e.g., by immunizing BALB/C mice with the human monoclonal antibodies according to the invention, and generating hybridomas from spleens of these mice by fusion with myeloma cells, such as NS1 cells, using standard techniques.

In yet another aspect, the invention provides a transgenic non-human animal, such as a transgenic mouse, which express human monoclonal antibodies that bind to IL-8. In a particular embodiment, the transgenic non-human animal is a transgenic mouse having a genome comprising a human heavy chain transgene and a human light chain transgene encoding all or a portion of an antibody of the invention. The transgenic non-human animal can be immunized with a purified or enriched preparation of IL-8 antigen, recombinant IL-8 antigen and/or cells expressing IL-8, including cells transfected with IL-8. Preferably, the transgenic non-human animal, e.g., the transgenic mouse, is capable of producing multiple isotypes of human monoclonal antibodies to IL-8 (e.g., IgG, IgA and/or IgM) by undergoing V-D-J recombination and isotype switching. Isotype switching may occur by, e.g., classical or non-classical isotype switching.

Accordingly, in yet another aspect, the invention provides isolated B cells from a transgenic non-human animal as described above, e.g., a transgenic mouse, which expresses human anti-IL-8 antibodies. The isolated B cells can then be immortalized by fusion to an immortalized cell to provide a source (e.g., a hybridoma) of human anti-IL-8 antibodies. Such hybridomas (i.e., which produce human anti-IL-8 antibodies) are also included within the scope of the invention.

As exemplified herein, human antibodies of the invention can be obtained directly from hybridomas which express the antibody, or can be cloned and recombinantly expressed in a fju'\m (e.g., a CHO cell, or a NS/0 cell). Further examples of host cells are HEK293 cells, plant cells, microorganisms, such as *E. coli*, and fungi, such as yeast. Alternatively, they can be produced recombinantly in a transgenic non-human animal or plant.

Accordingly, in yet another aspect, the invention provides nucleic acid molecules encoding human anti-IL-8 antibodies, as well as recombinant expression vectors which include the nucleic acids of the invention, and host cells transfected with such vectors. Methods of producing the antibodies by culturing these host cells are also encompassed by the invention. Particular nucleic acids provided by the invention comprise the nucleotide sequences shown in SEQ ID NO:10 and SEQ ID NO:6, encoding to the heavy and light chains respectively of 10F8.

Other features and advantages of the instant invention will be apparent from the following detailed description and examples which should not be construed as limiting.

BRIEF DESCRIPTION OF THE DRAWINGS

FIG. 1 shows the nucleotide sequences of the $V_L$- and $V_H$-regions (SEQ ID NOs:1 and 3), respectively, from HuMab 10F8. Leader sequences are underlined.

FIG. 2 is an alignment comparison of the nucleotide sequence of the light (kappa) chain V region of HuMab 10F8 (SEQ ID NO:6) and the corresponding Vκ A-27 germline nucleotide sequence (SEQ ID NO:5).

FIG. 3 is an alignment comparison of the amino acid sequence of the light (kappa) chain V region of HuMab 10F8 (SEQ ID NO:8) and the corresponding Vκ A-27 germline-encoded amino acid sequence (SEQ ID NO:7).

FIG. 4 is an alignment comparison of the nucleotide sequence of the heavy chain V region of HuMab 10F8 (SEQ ID NO:10) and the corresponding $V_H$ 3-33 germline nucleotide sequence (SEQ ID NO:9).

FIG. 5 is an alignment comparison of the amino acid sequence of the heavy chain V region of HuMab 10F8 (SEQ ID NO:12) and the corresponding $V_H$ 3-33 germline-encoded amino acid sequence (SEQ ID NO:11).

DETAILED DESCRIPTION OF THE INVENTION

Figure 6:
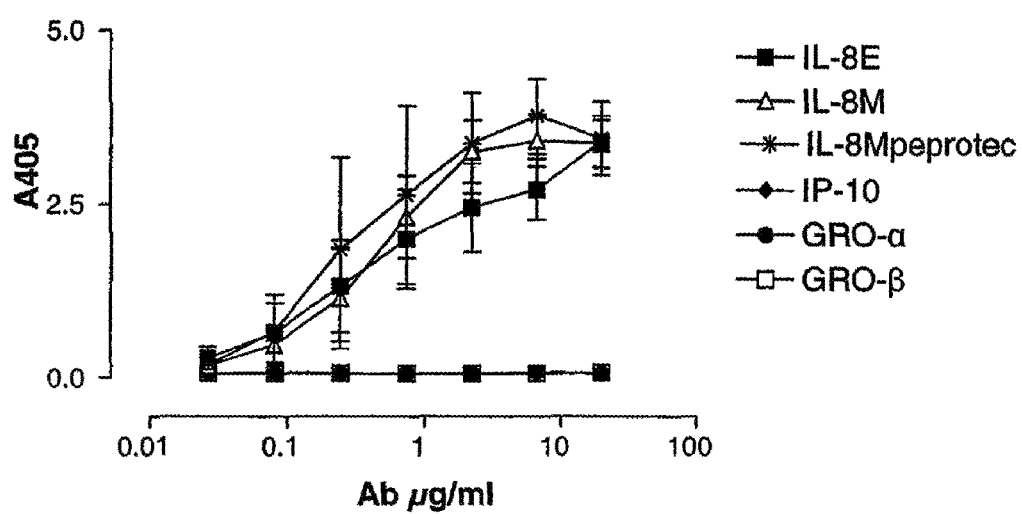
FIG. 6 is a graph showing that HuMab 10F8 binds to both endothelial cell derived and monocyte derived IL-8, but that it does not bind to IP-10, GRO-α or GRO-β.

The present invention provides improved human antibodies which bind to human IL-8 and antibody-based therapies for treating and diagnosing a variety of disorders mediated by IL-8 (e.g., disorders caused by the proinflammatory effects and the angiogenic effects of IL-8). As used herein, the term "proinflammatory effects" includes any humoral or cell-mediated immune response induced by IL-8, such as the chemotactic activity for leukocytes. The term "angiogenic effects of IL-8" includes the growth of new blood vessels or the vascularization of tumor cells induced by IL-8. Therapies of the invention employ human monoclonal antibodies which bind to and inhibit such functions of IL-8, particularly in human therapy.

In one embodiment the antibody is an IgG1 antibody, more particularly an IgG1,κ or IgG1,λ, isotype. In another embodiment the antibody is an IgG3 antibody, more particularly an IgG3,κ or IgG3,λ isotype. In yet another embodiment the antibody is an IgG4 antibody, more particularly an IgG4,κ or IgG4,λ isotype. In still another embodiment the antibody is an IgA1 or IgA2 antibody. In yet a further embodiment the antibody is an IgM antibody.

In one embodiment, the human antibodies are produced in a non-human transgenic animal, e.g., a transgenic mouse, capable of producing multiple isotypes of human monoclonal antibodies to IL-8 (e.g., IgG, IgA and/or IgE) by undergoing V-D-J recombination and isotype switching. Such transgenic animal can also be a transgenic rabbit for producing polyclonal antibodies such as disclosed in US 2003/0017534. Accordingly, the invention also encompasses human polyclonal antibodies which specifically bind to IL-8. Accordingly, particular aspects of the invention include not only antibodies, antibody fragments, and pharmaceutical compositions thereof, but also non-human transgenic animals, B cells, hybridomas, and transfectomas which produce monoclonal antibodies. Methods of using the antibodies of the invention to detect a cell producing IL-8, either in vitro or in vivo, are also encompassed by the invention. Methods of using the antibodies of the invention to block or inhibit IL-8 induced activities, e.g., proinflammatory activities, chemotactic activities, and angiogenesis are also provided and are useful in the treatment of disorders associated with IL-8.

In one embodiment, the human antibodies of the invention can be used in methods for treating inflammatory or hyperproliferative skin disorders, such as pustulosis palmoplantaris (PPP), psoriasis, including plaque psoriasis and guttate type psoriasis, bullous skin diseases, such as bullous pemphigoid, contact dermatitis, eczema, erythematosus, and atopic dermatitis.

In another embodiment, the human antibodies of the invention can be used in methods for treating immune, autoimmune, inflammatory or infectious diseases, such as psoriatic arthritis, systemic scleroderma and sclerosis, inflammatory bowel disease (IBD), Crohn's disease, ulcerative colitis, acute lung injury, such as acute respiratory distress syndrome or adult respiratory distress syndrome, meningitis, encephalitis, uveitis, multiple myeloma, glomerulonephritis, nephritis, asthma, atherosclerosis, leukocyte adhesion deficiency, multiple sclerosis, Raynaud's syndrome, Sjögren's syndrome, juvenile onset diabetes, Reiter's disease, Behcet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, lupus erythematosus, rheumatoid arthritis (RA), ankylosing spodylitis, pemphigus, Graves' disease, Hashimoto's thyroiditis, small vessel vasculitides, such as Wegener's granulomatosis, Omen's syndrome, chronic renal failure, autoimmune thyroid disease, acute infectious mononucleosis, HIV, herpes virus associated diseases, human virus infections, such as common cold as caused by human rhinovirus, coronavirus, other enterovirus, herpes virus, influenza virus, parainfluenza virus, respiratory syncytial virus or adenovirus infection, bacteria pneumonia, wounds, sepsis, cerebral stroke/cerebral edema, ischaemia-reperfusion injury and hepatitis C.

In one embodiment, the human monoclonal antibodies can be used for the treatment of ischaemia-reperfusion injury after thrombolysis, cardiopulmonary bypass, percutaneous coronary intervention (PCI), coronary artery bypass, or cardiac transplantation.

In yet another embodiment, the human antibodies of the invention can be used for treatment of alcoholic hepatitis and acute pancreatitis.

In yet a further embodiment, the human antibodies of the invention can be used in methods for treating diseases involving IL-8 mediated angiogenesis, such as tumors and cancers, e.g., melanoma, thyroid carcinoma, transitional cell carcinoma, trichilemmona, squamous cell carcinoma and breast cancer.

In another embodiment, the human antibodies of the invention can be used for treating diseases wherein blocking of granulocyte migration is beneficial, e.g., in diseases affecting the central nervous system, such as isolated cerebral angiitis;

diseases affecting the peripheral nervous system, such as mononeuritis multiplex;

cardiovascular disorders, such as acute myocardial infarction, myocarditis, pericarditis, and Liebman-Sachs endocarditis;

pulmonary disorders, such as chronic obstructive pulmonary disease (COPD), alveolitis, obliterating bronchiolitis, cystic fibrosis, allergic aspergillosis, and Löfflers syndrome;

hepatic disorders, such as sclerosing cholangiolitis;

urogenital disorders, such as chronic cyctitis;

renal disorders, such as tubulo-interstial nephritis;

infectious diseases, such as severe acute respiratory syndrome (SARS);

rheumatic disorders, such as large vessel vasculitides (including giant cell arteritis, polymyalgia rheumatica, and Takayasu arteritis), medium-sized vessel vasculitides (including polyarteritis *nodosa*, localized polyarteritis *nodosa*, and Kawasaki disease), small vessel vasculitides (including Churg-Strauss syndrome, microscopic polyarteritis, cryoglobulinemic vasculitis, and leucocytoclastic angiitis), secondary vasculitides (including rheumatoid vasculitis, and vasculitis associated with systemic lupus erythematosus or Sjögren's syndrome), isolated sacroileitis, the SAPHO syndrome, and disciitis (including postoperative disciitis);

endocrine disorders, such as subacute thyroiditis;

skin disorders, such as cicatricial pemphigoid, dermatitis herpetiformis, subcorneal pustular dermatosis, epidermolysis bullosa acquisita, rosacea, acute febrile dermatosis, granuloma annulare (including Sweet's syndrome), pyoderma gangraenosum, and acne (including acne conglobata);

connective tissue disorders, such as sarcoidosis, relapsing polychondritis, familial Mediterranean fever, panniculitis, erythema nodosum, Weber-Christian's disease, and retroperitoneal fibrosis.

In another embodiment, the human antibodies of the invention are used for treating diseases wherein interfering with interactions between IL-8 and osteoclasts is beneficial, such as osteoporosis, and osteolytic metastases.

In another embodiment, the human antibodies of the invention are used for treating disease wherein interfering with interactions between IL-8 and tumor cells is beneficial, such as gastric cancer, colorectal cancer, and urine bladder cancer.

In order that the present invention may be more readily understood, certain terms are first defined. Additional definitions are set forth throughout the detailed description.

The terms "IL-8," "IL-8 antigen" and "Interleukin 8" are used interchangeably herein, and include any variants or isoforms which are naturally expressed by cells or are expressed by cells transfected with the IL-8 gene.

The term "antibody" as referred to herein includes intact antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to bind to an antigen (e.g., IL-8). It has been shown that the antigen-binding function of an antibody can be performed by fragments of an intact antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR), e.g., $V_H$ CDR3. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region is preferably modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost by treatment with denaturing solvents.

As used herein, the terms "inhibits binding" and "blocks binding" (e.g., referring to inhibition/blocking of binding of IL-8 to its receptors, CXCR1 and CXCR2) are used interchangeably and encompass both partial and complete inhibition/blocking. The inhibition/blocking of IL-8 preferably reduces or alters the normal level or type of activity that occurs when IL-8 binding occurs without inhibition or blocking, e.g., inhibition of IL-8 induced elastase release or calcium flux or inhibition of IL-8 induced increased expression of CD11b (Mac-1) and decreased expression of L-selectin. Inhibition and blocking are also intended to include any measurable decrease in the binding affinity of IL-8 when in contact with an anti-IL-8 antibody as compared to IL-8 not in contact with an anti-IL-8 antibody, e.g., the blocking of binding of IL-8 to its receptor by at least about 10%, 20%, 30%, 40%, 50%, 60%, 70%, 80%, 90%, 99%, or 100%.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody", as used herein, is intended to include all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody," as used herein, is intended to refer to an antibody which is substantially free of other antibodies having different antigenic specificities (e.g., an isolated antibody that binds to IL-8 is substantially free of antibodies that bind antigens other than IL-8). An isolated antibody that binds to an epitope, isoform or variant of human IL-8 may, however, have cross-reactivity to other related antigens, e.g., from other species (e.g., IL-8 species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to antibody binding to a predetermined antigen. Typically, the antibody binds with an affinity corresponding to a $K_D$ of about $10^{-8}$ M or less, and binds to the predetermined antigen with an affinity (as expressed by $K_D$) that is at least 10 fold less, and preferably at least 100 fold less than its affinity for binding to a non-specific antigen (e.g., BSA, casein) other than the predetermined antigen or a closely-related antigen. Alternatively, the antibody can bind with an affinity corresponding to a $K_A$ of about $10^7$ $M^{-1}$ or higher, and binds to the predetermined antigen with an affinity (as expressed by $K_A$) that is at least 10 fold higher, and preferably at least 100 fold higher than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

The term "$k_d$" (sec$^{-1}$), as used herein, is intended to refer to the dissociation rate constant of a particular antibody-antigen interaction. Said value is also referred to as the $k_{off}$ value.

The term "$k_D$" (M$^{-1}$×sec$^{-1}$), as used herein, is intended to refer to the association rate constant of a particular antibody-antigen interaction.

The term "$K_A$" (M), as used herein, is intended to refer to the association equilibrium constant of a particular antibody-antigen interaction.

The term "$K_D$" (M$^{-1}$), as used herein, is intended to refer to the dissociation equilibrium constant of a particular antibody-antigen interaction.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the $C_H$ gene encoding the non-switched isotype is typically the first $C_H$ gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human σ$_\mu$ and human Σ$_\mu$ (δ-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a µ switch region, will be 5' (i.e., upstream) of the construct region to be deleted during the switch recombination. The "switch acceptor" region will be between the construct region to be deleted and the replacement constant region (e.g., γ, ε, etc.).

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the non-human transgenic animal, when one of ordinary skill in the art would recognize the glycosylation pattern of the heterologous antibody as being more similar to said pattern of glycosylation in the species of the non-human transgenic animal than to the species from which the $C_H$ genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding intact antibodies or antibody portions (e.g., $V_H$, $V_L$, CDR3) that bind to IL-8, is intended to refer to a nucleic acid molecule in which the nucleotide sequences encoding the intact antibody or antibody portion are free of other nucleotide sequences encoding intact antibodies or antibody portions that bind antigens other than IL-8, which other sequences may naturally flank the nucleic acid in human genomic DNA. In one embodiment, the human anti-IL-8 antibody includes the amino acid sequence of 10F8, as well as heavy chain ($V_H$) and light chain ($V_L$) variable amino acid regions having the sequences shown in SEQ ID NOs:12 and 8 or encoded by the nucleotide sequences shown in SEQ ID NOs: 10 and 6.

The present invention also encompasses "derivatives" of the amino acid sequences as set forth in SEQ ID NO: 8 or 12, wherein one or more of the amino acid residues have been derivatised, e.g., by acylation or glycosylation, without significantly affecting or altering the binding characteristics of the antibody containing the amino acid sequences.

Furthermore, the present invention comprises antibodies in which one or more alterations have been made in the Fc region in order to change functional or pharmacokinetic properties of the antibodies. Such alterations may result in a decrease or increase of C1q binding and CDC (complement dependent cytotixicity) or of FcγR binding and antibody-dependent cellular cytotoxicity (ADCC). Substitutions can for example be made in one or more of the amino acid positions 234, 235, 236, 237, 297, 318, 320, and 322 of the heavy chain constant region, thereby causing an alteration in an effector function while retaining binding to antigen as compared with the unmodified antibody, cf. U.S. Pat. No. 5,624,821 and U.S. Pat. No. 5,648,260. Further reference may be had to WO 00/42072 disclosing antibodies with altered Fc regions that increase ADCC, and WO 94/29351 disclosing antibodies having mutations in the N-terminal region of the CH2 domain that alter the ability of the antibodies to bind to FcRI and thereby decreases the ability of the antibodies to bind to C1q which in turn decreases the ability of the antibodies to fix complement. Furthermore, Shields et al., *J. Biol. Chem.* (2001) 276:6591-6604 teaches combination variants, e.g., T256A/S298A, S298A/E333A, and S298A/E333A/K334A, that improve FcγRIII binding.

The in vivo half-life of the antibodies can also be improved by modifying the salvage receptor epitope of the Ig constant domain or an Ig-like constant domain such that the molecule does not comprise an intact CH2 domain or an intact Ig Fc region, cf. U.S. Pat. No. 6,121,022 and U.S. Pat. No. 6,194,551. The in vivo half-life can furthermore be increased by making mutations in the Fc region, e.g., by substituting threonine for leucine at position 252, threonine for serine at position 254, or threonine for phenylalanine at position 256, cf. U.S. Pat. No. 6,277,375.

Furthermore, the glycosylation pattern of the antibodies can be modified in order to change the effector function of the antibodies. For example, the antibodies can be expressed in a transfectoma which does not add the fucose unit normally attached to the carbohydrate attached to Asn at position 297 of Fc in order to enhance the affinity of Fc for FcγRIII which in turn will result in an increased ADCC of the antibodies in the presence of NK cells, cf. Shield et al. (2002) *J. Biol. Chem.*, 277:26733. Furthermore, modification of galactosylation can be made in order to modify CDC. Further reference may be had to WO 99/54342 and Umana et al., *Nat. Biotechnol.* (1999) 17:176 disclosing a CHO cell line engineered to express GntIII resulting in the expression of monoclonal antibodies with altered glycoforms and improved ADCC activity.

Furthermore, the antibody fragments, e.g., Fab fragments, of the invention can be pegylated to increase the half-life. This can be carried out by pegylation reactions known in the art, as described, for example, in *Focus on Growth Factors* (1992) 3:4-10, EP 154 316 and EP 401 384.

Accordingly, the invention includes antibodies encoded by the (heavy and light chain variable region) nucleotide sequences disclosed herein and/or containing the (heavy and light chain variable region) amino acid sequences disclosed herein (i.e., SEQ ID NOs: 10, 6, 12, and 8).

For nucleic acid and amino acid sequences, the term "homology" indicates the degree of identity between two sequences, when optimally aligned and compared, with appropriate insertions or deletions. Alternatively, substantial homology exists when the DNA segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the website for Accelrys GCG, gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available on the website for Accelrys GCG, gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See the website of the National Center for Biotechnology Information (NCBI), National Library of Medicine, Building 38A, Bethesda, Md. 20894, U.S.A., ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

The nucleic acid compositions of the present invention, while often in a native sequence (except for modified restriction sites and the like), from either cDNA, genomic or mixtures thereof may be mutated in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby be replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells, and NS/0 cells.

The term "transfectoma", as used herein, includes a recombinant eukaryotic host cell expressing the antibody, such as CHO cells, NS/0 cells, HEK293 cells, plant cells, or fungi, including yeast cells.

As used herein, the term "subject" includes any human or non-human animal. The term "non-human animal" includes all vertebrates, e.g., mammals and non-mammals, such as non-human primates, sheep, dogs, cows, chickens, amphibians, reptiles, etc.

The terms "transgenic, non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-IL-8 antibodies when immunized with IL-8 antigen and/or cells expressing IL-8. The human heavy chain transgene can be integrated into the chromosomal DNA of the mouse, as is the case for transgenic, e.g., HuMAb mice, or the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to IL-8 (e.g., IgG, IgA and/or IgE) by undergoing V-D-J recombination and isotype switching. Transgenic, non-human animals can also be used for production of a specific anti-IL-8 antibody by introducing genes encoding such specific anti-IL-8 antibody, for example by operatively linking the genes to a gene which is expressed in the milk of the animal.

Various aspects of the invention are described in further detail in the following subsections.

I. Production of Human Antibodies to IL-8

The human monoclonal antibodies of the invention can be produced by a variety of techniques, including conventional monoclonal antibody methodology e.g., the standard somatic cell hybridization technique of Kohler and Milstein (1975) Nature 256:495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

In a preferred embodiment, human monoclonal antibodies directed against IL-8 can be generated using transgenic mice carrying parts of the human immune system rather than the mouse system. These transgenic mice, referred to herein as "HuMAb" mice, contain a human immunoglobulin gene miniloci that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg, et al. (1994) Nature 368(6474):856-859). Accordingly, the mice exhibit reduced expression of mouse IgM or $\kappa$ light chain, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. Vol. 13:65-93, and Harding, F. and Lonberg, N. (1995) Ann. N.Y. Acad. Sci. 764:536-546). The preparation of HuMAb mice is described in detail Section II below and in Taylor, L. et al. (1992) Nucleic Acids Research 20:6287-6295; Chen, J. et al. (1993) International Immunology 5:647-656; Tuaillon et al. (1993) Proc. Natl. Acad. Sci. USA 90:3720-3724; Choi et al. (1993) Nature Genetics 4:117-123; Chen, J. et al. (1993) EMBO J. 12:821-830; Tuaillon et al. (1994) J. Immunol. 152:2912-2920; Lonberg, N. et al., (1994) Nature 368(6474):856-859; Lonberg, N. (1994) Handbook of Experimental Pharmacology 113:49-101; Taylor, L. et al. (1994) International Immunology 6:579-591; Lonberg, N. and Huszar, D. (1995) Intern. Rev. Immunol. Vol. 13:65-93; Harding, F. and Lonberg, N. (1995) Ann. N.Y. Acad. Sci. 764:536-546; Fishwild, D. et al. (1996) Nature Biotechnology 14:845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg, N. and Kay, R. M. and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; and WO 92/03918, published Mar. 19, 1992. Preferred HuMAb mice have a JKD disruption in their endogenous light chain (kappa) genes (as described in Chen et al. (1993) EMBO J. 12: 821-830), a CMD disruption in their endogenous heavy chain genes (as described in Example 1 of WO 01/14424 by Korman et al.), a KCo5 human kappa light chain transgene (as described in Fishwild et al. (1996) Nature Biotechnology 14:845-851), and a HCo7 human heavy chain transgene (as described in U.S. Pat. No. 5,770,429 by Lonberg, N. and Kay, R. M.) and/or a HCo12 human heavy chain transgene (as described in Example 2 of WO 01/14424 by Korman et al.).

Alternatively, mice carrying human immunoglobulin genes on a transchromosomic fragment can be used to generate anti-IL-8 antibodies. Preparation of such transchromosomic mice are described in WO 97/07671 by Tomizuka et al. A preferred mouse is one in which certain human immunoglobulin genes are carried on a transgene and others are carried on a transchromosome, such as a mouse carrying a human light chain transgene (e.g., the KCo5 kappa chain transgene) and a human heavy chain transchromosome (e.g, the SC20 transchromosome) as described in detail in WO 02/43478 by Ishida et al.

HuMAb Immunizations

To generate fully human monoclonal antibodies to IL-8, HuMAb mice can be immunized with a purified or enriched preparation of IL-8 antigen and/or cells producing IL-8 and/or recombinant IL-8, as described by Lonberg, N. et al. (1994) *Nature* 368(6474):856-859; Fishwild, D. et al. (1996) *Nature Biotechnology* 14:845-851 and WO 98/24884. Preferably, the mice will be 6-16 weeks of age upon the first infusion. For example, recombinant IL-8 can be used to immunize the HuMAb mice intraperitoneally.

Cumulative experience with various antigens has shown that the HuMAb transgenic mice respond best when initially immunized intraperitoneally (IP) with antigen in complete Freund's adjuvant, followed by every other week i.p. immunizations (up to a total of 6) with antigen in incomplete Freund's adjuvant. The immune response can be monitored over the course of the immunization protocol with plasma samples being obtained by retroorbital bleeds. The plasma can be screened by ELISA (as described below), and mice with sufficient titers of anti-IL-8 human immunoglobulin can be used for fusions. Mice can be boosted intravenously with antigen 3 days before sacrifice and removal of the spleen. It is expected that 2-3 fusions for each antigen may need to be performed. Several mice will be immunized for each antigen. For example, a total of twelve HuMAb mice of the HCo7 and HCo12 strains can be immunized.

Generation of Hybridomas Producing Human Monoclonal Antibodies to IL-8

The mouse splenocytes can be isolated and fused with PEG to a mouse myeloma cell line based upon standard protocols. The resulting hybridomas are then screened for the production of antigen-specific antibodies. For example, single cell suspensions of splenic lymphocytes from immunized mice are fused to one-sixth the number of P3X63-Ag8.653 nonsecreting mouse myeloma cells (ATCC, CRL 1580) with 50% PEG. Cells are plated at approximately $2\times10^5$ in flat bottom microtiter plates, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/mL penicillin, 50 mg/mL streptomycin, 50 mg/mL gentamycin and 1×HAT (Sigma; the HAT is added 24 hours after the fusion). After two weeks, cells are cultured in medium in which the HAT is replaced with HT. Individual wells are then screened by ELISA for human anti-IL-8 monoclonal IgM and IgG antibodies. Once extensive hybridoma growth occurs, medium is observed usually after 10-14 days. The antibody secreting hybridomas are replated, screened again, and if still positive for human IgG, anti-IL-8 monoclonal antibodies, can be subcloned at least twice by limiting dilution. The stable subclones are then cultured in vitro to generate small amounts of antibody in tissue culture medium for characterization.

Generation of Transfectomas Producing Human Monoclonal Antibodies to IL-8

Human antibodies of the invention also can be produced in a host cell transfectoma using, for example, a combination of recombinant DNA techniques and gene transfection methods as is well known in the art (Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include CHO cells (including dhfr-CHO cells, described in Urlaub and Chasin, (1980) *Proc. Natl. Acad. Sci.* USA 77:4216-4220, used with a DHFR selectable marker, e.g., as described in R. J. Kaufman and P. A. Sharp (1982) *Mol. Biol.* 159:601-621), NS/0 myeloma cells, COS cells, HEK293 cells and SP2.0 cells. In particular for use with NS/0 myeloma cells, another preferred expression system is the GS (glutamine synthetase) gene expression system disclosed in WO 87/04462, WO 89/01036 and EP 338 841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Further Recombinant Means for Producing Human Monoclonal Antibodies to IL-8

Alternatively the cloned antibody genes can be expressed in other expression systems, including prokaryotic cells, such as microorganisms, e.g., *E. coli* for the production of scFv antibodies, algi, as well as insect cells. Furthermore, the antibodies can be produced in transgenic non-human animals, such as in milk from sheep and rabbits or eggs from hens, or in transgenic plants. See, e.g., Verma, R., et al. (1998). Antibody engineering: Comparison of bacterial, yeast, insect and mammalian expression systems. *J. Immunol. Meth.* 216:165-181; Pollock, et al. (1999). Transgenic milk as a method for the production of recombinant antibodies. *J. Immunol. Meth.* 231:147-157; and Fischer, R., et al. (1999). Molecular farming of recombinant antibodies in plants. *Biol. Chem.* 380:825-839.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, *Nature* 332:323-327; Jones, P. et al., 1986, *Nature* 321:522-525; and Queen, C. et al., 1989, *Proc. Natl. Acad. See.* U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody which contains mutations throughout the variable gene but typically clustered in the CDRs. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see WO 99/45962). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion of particular restriction sites, or optimization of particular codons.

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak (1991) *J. Biol. Chem.* 266: 19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site of the gamma heavy chain) in the PCR amplification to generate fragments that can easily be cloned into the expression vector constructs.

The reconstructed heavy and light chain variable regions are then combined with cloned promoter, leader sequence, translation initiation, constant region, 3' untrans-lated, polyadenylation, and transcription termination sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human IgG1,κ or IgG4,κ antibodies. Similar plasmids can be constructed for expression of other heavy chain isotypes, or for expression of antibodies comprising lambda light chains.

Thus, in another aspect of the invention, the structural features of a human anti-IL-8 antibody of the invention, e.g., 10F8, are used to create structurally related human anti-IL-8 antibodies that retain at least one functional property of the antibodies of the invention, such as binding to IL-8. More specifically, one or more CDRs of 10F8 can be combined recombinantly with known human framework regions and CDRs to create additional, recombinantly-engineered, human anti-IL-8 antibodies of the invention.

Accordingly, in another embodiment, the invention provides a method for preparing an anti-IL-8 antibody comprising:

preparing an antibody comprising (1) human heavy chain framework regions and human heavy chain CDRs, wherein at least one of the human heavy chain CDRs comprises an amino acid sequence selected from the amino acid sequences of CDRs shown in FIG. 5 (SEQ ID NOs: 22, 23, or 24); and (2) human light chain framework regions and human light chain CDRs, wherein at least one of the light chain CDRs comprises an amino acid sequence selected from the amino acid sequences of CDRs shown in FIG. 3 (SEQ ID NOs: 16, 17, or 18);

wherein the antibody retains the ability to bind to IL-8. The ability of the antibody to bind IL-8 can be determined using standard binding assays, such as those set forth in the Examples (e.g., an ELISA).

Since it is well known in the art that antibody heavy and light chain CDR3 domains play a particularly important role in the binding specificity/affinity of an antibody for an antigen, the recombinant antibodies of the invention prepared, as set forth above, preferably comprise the heavy and light chain CDR3s of 10F8. The antibodies further can comprise the CDR2s of 10F8. The antibodies further can comprise the CDR1s of 10F8. The antibodies can further comprise any combinations of the CDRs.

Accordingly, in another embodiment, the invention further provides anti-IL-8 antibodies comprising: (1) human heavy chain framework regions, a human heavy chain CDR1 region, a human heavy chain CDR2 region, and a human heavy chain CDR3 region, wherein the human heavy chain CDR3 region is the heavy chain CDR3 of 10F8 as shown in FIG. 5 (SEQ ID NO: 24); and (2) human light chain framework regions, a human light chain CDR1 region, a human light chain CDR2 region, and a human light chain CDR3 region, wherein the human light chain CDR3 region is the light chain CDR3 of 10F8 as shown in FIG. 3 (SEQ ID NO: 18), wherein the antibody binds IL-8. The antibody may further comprise the heavy chain CDR2 and/or the light chain CDR2 of 10F8. The antibody may further comprise the heavy chain CDR1 and/or the light chain CDR1 of 10F8.

The CDR1, 2, and/or 3 regions of the engineered antibodies described above can comprise the exact amino acid sequence(s) as those of 10F8 disclosed herein. However, the ordinarily skilled artisan will appreciate that some deviation from the exact CDR sequences of 10F8 may be possible while still retaining the ability of the antibody to bind IL-8 effectively. Accordingly, in another embodiment, the engineered antibody may be composed of one or more CDRs that are 95%, 98% or 99.5% identical to one or more CDRs of 10F8.

Accordingly, in another embodiment, the invention provides anti-IL-8 antibodies comprising a heavy chain variable region and/or a light chain variable region which is homologous to or derived from its corresponding germline variable region sequence, e.g., the Vκ A-27 germline nucleotide and amino acid sequences shown in FIGS. 2 and 3 (SEQ ID NOs:5 and 7, respectively) and/or the $V_H$ 3-33 germline nucleotide and amino acid sequences shown in FIGS. 4 and 5 (SEQ ID NOs:9 and 11, respectively), and retains at least one functional property of the antibodies of the invention, such as binding to IL-8.

Other particular antibodies of the invention bind to human IL-8 and comprise a light chain variable region having an amino acid sequence which is at least about 94% identical, preferably about 96%, more preferably about 97%, 98%, or 99% identical to the germline amino acid sequence shown in FIG. 3 (SEQ ID NO:7) and/or a heavy chain variable region having an amino acid sequence which is at least about 92% identical, preferably about 94%, more preferably about 96%, 97%, 98%, or 99% identical to the amino acid sequence shown in FIG. 5 (SEQ ID NO:11). Alternatively, the antibodies may comprise a light chain variable region encoded by a nucleotide sequence which is at least about 94% identical, preferably about 96%, more preferably about 97%, 98%, or 99% identical to the germline nucleotide sequence shown in FIG. 2 (SEQ ID NO:5) and/or a heavy chain variable region encoded by a nucleotide sequence which is at least about 92% identical, preferably about 94%, more preferably about 96%, 97%, 98%, or 99% identical to the nucleotide sequence shown in FIG. 4 (SEQ ID NO:9).

Particular antibodies of the invention also include human antibodies which bind to human IL-8 and comprise a light chain variable region derived from the Vκ A-27 germline amino acid sequence as shown in FIG. 3 (SEQ ID NO:7) and have an amino acid sequence which comprises at least one residue selected from the group consisting of an isoleucine at position 29, a proline residue at position 52, an alanine residue at position 93, a glycine residue at position 94, a leucine residue at position 96, a proline residue at position 100, an aspartic acid at position 105, as shown in FIG. 3, and any combination thereof. Alternatively or in addition, the antibodies may comprise a heavy chain variable region derived from the $V_H$ 3-33 germline amino acid sequence as shown in FIG. 5 (SEQ ID NO:11) and have an amino acid sequence which comprises at least one residue selected from the group consisting of an glutamine at position 3, a histidine residue at position 31, a tyrosine residue at position 35, an isoleucine residue at position 51, a tyrosine residue at position 57, an asparagine residue at position 60, an alanine residue at position 61, an isoleucine residue at position 70, an asparagine residue at position 74, a glutamine residue at position 82, an arginine residue at position 100, a leucine residue at position 103, as shown in FIG. 5, and any combination thereof.

In another embodiment, the invention provides human anti-IL-8 antibodies which comprise a CDR domain having a human heavy and light chain CDR1 region, a human heavy and light chain CDR2 region, and a human heavy and light chain CDR3 region, wherein the CDR1, CDR2, and CDR3 heavy chain regions are derived from the $V_H$ 3-33 germline amino acid sequence as shown in FIG. 5 (SEQ ID NO:11) or wherein the CDR1, CDR2, and CDR3 light chain regions are derived from the Vκ A-27 germline amino acid sequence as shown in FIG. 3 (SEQ ID NO:7), and wherein (a) the CDR1 human heavy chain region comprises a histidine and a tyrosine residue at positions 1 and 5, respectively, as shown in FIG. 5 (SEQ ID NO:22);

(b) the CDR2 human heavy chain region comprises an isoleucine, tyrosine, asparagine, and alanine residue at positions 2, 8, 11, and 12, respectively, as shown in FIG. 5 (SEQ ID NO:23);

(c) the CDR3 human heavy chain region comprises an arginine and leucine residue at positions 2 and 5, respectively, as shown in FIG. 5 (SEQ ID NO:24);

(d) the CDR1 human light chain region comprises an isoleucine residue at position 6, as shown in FIG. 3 (SEQ ID NO:16);

(e) the CDR2 human light chain region comprises a proline residue at position 2, as shown in FIG. 3 (SEQ ID NO:17);

(f) the CDR3 human light chain region comprises a tyrosine, alanine, glycine, and leucine residue at positions 3, 4, 5, and 6, respectively, as shown in FIG. 3 (SEQ ID NO:18); and (g) any combination of (a), (b), (c), (d), (e), or (f).

In another embodiment, the human antibodies may comprise a human heavy and light chain CDR1 region, a human heavy and light chain CDR2 region, and a human heavy and light chain CDR3 region, wherein the CDR1, CDR2, and CDR3 heavy chain regions are derived from the $V_H$ 3-33 germline amino acid sequence as shown in FIG. 5 (SEQ ID NO:11) and/or wherein the CDR1, CDR2, and CDR3 light chain regions are derived from the Vκ A-27 germline amino acid sequence as shown in FIG. 3 (SEQ ID NO:7), and wherein at least one of the CDR domains is selected from the group consisting of:

(a) a light chain CDR1 region comprising an amino acid sequence which is at least 92% identical to the amino acid sequence shown in FIG. 3 (SEQ ID NO:16);

(b) a light chain CDR2 region comprising an amino acid sequence which is at least 86% identical to the amino acid sequence shown in FIG. 3 (SEQ ID NO:17);

(c) a light chain CDR3 region comprising an amino acid sequence which is at least 43% identical to the amino acid sequence shown in FIG. 3 (SEQ ID NO:18);

(d) a heavy chain CDR1 region comprising an amino acid sequence which is at least 61% identical to the amino acid sequence shown in FIG. 5 (SEQ ID NO:22);

(e) a heavy chain CDR2 region comprising an amino acid sequence which is at least 77% identical to the amino acid sequence shown in FIG. 5 (SEQ ID NO:23); and (f) a heavy chain CDR3 region comprising an amino acid sequence which is at least 76% identical to the amino acid sequence shown in FIG. 5 (SEQ ID NO:24); and (g) any combination of (a), (b), (c), (d), (e), or (f).

In yet another embodiment, at least one of the CDR domains of the human antibodies comprises an amino acid sequence selected from the group consisting of:

(a) the amino acid sequence of the light chain CDR1 region comprises an isoleucine residue at position 6, as shown in FIG. 3 (SEQ ID NO:16);

(b) the amino acid sequence of the light chain CDR2 region comprises a proline residue at position 2, as shown in FIG. 3 (SEQ ID NO:17);

(c) the amino acid sequence of the light chain CDR3 region comprises a tyrosine residue at position 3, an alanine residue at position 4, a glycine residue at position 5, and a leucine residue at position 7, as shown in FIG. 3 (SEQ ID NO:18);

(d) the amino acid sequence of the heavy chain CDR1 region comprises a histidine residue at position 1, and a tyrosine residue at position 5, as shown in FIG. 5 (SEQ ID NO:22);

(e) the amino acid sequence of the heavy chain CDR2 region comprises an isoleucine residue at position 2, a tyrosine residue at position 8, an asparagine residue at position 11, and an alanine residue at position 12, as shown in FIG. 5 (SEQ ID NO:23);

(f) the amino acid sequence of the heavy chain CDR3 region comprises an arginine residue at position 2 and a leucine residue at position 5, as shown FIG. 5 (SEQ ID NO:24); and (g) any combination of (a), (b), (c), (d), (e), or (f).

In another embodiment the invention relates to an isolated human monoclonal antibody which binds to human IL-8 comprising a $V_L$ CDR3 domain having the amino acid sequence:

Gln-Gln-Tyr-$X_1$-$X_2$-Ser-$X_3$-Thr (SEQ ID NO: 46), wherein $X_1$, $X_2$ and $X_3$ each represents a natural amino acid residue, and $X_1$ is different from Gly, or $X_2$ is different from Ser, or $X_3$ is different from Pro.

In one embodiment $X_1$ is different from Gly, $X_2$ is different from Ser, and $X_3$ is different from Pro.

In a further embodiment $X_1$ is Ala, and $X_2$ and $X_3$ are independently Gly, Ala, Val, Leu, or Ile.

In yet another embodiment the invention relates to an isolated human monoclonal antibody which binds to human IL-8 comprising a $V_H$ CDR3 domain having the amino acid sequence:

Asp-$X_4$-Val-Gly-$X_5$-Phe-Asp-Tyr (SEQ ID NO: 47), wherein $X_4$ is Lys, Arg, or His, and $X_5$ is Gly, Ala, Val, Leu, or Ile.

In still another embodiment the invention relates to an isolated human monoclonal antibody which binds to human IL-8 comprising a $V_L$ CDR3 domain as disclosed in the above embodiments and a $V_H$ CDR3 domain as disclosed in the above embodiments.

In addition, or alternative, to simply binding IL-8, antibodies such as those described above may be selected for their retention of other functional properties of antibodies of the invention, such as:

(1) binding to human IL-8 and inhibiting IL-8 induced proinflammatory effects;

(2) inhibiting binding of IL-8 to its receptors on neutrophils;

(3) inhibiting IL-8 induced chemotactic activity for neutrophils;

(4) inhibiting IL-8 induced calcium flux;

(5) inhibiting IL-8 induced changes in expression levels of adhesion molecules on neutrophils;

(6) binding to human IL-8 and inhibiting IL-8 induced increased expression of CD11b (Mac-1) and decreased expression of L-selectin on neutrophils;

(7) not cross-reacting with related chemokines, such as human GRO-α, human GRO-β, human IP-10 and human NAP-2;

(8) binding to human IL-8 with a dissociation equilibrium constant ($K_D$) of approximately $10^{-8}$ M or less, such as $10^{-9}$ M or less, $10^{-19}$ M or less, or $10^{-11}$ M or even less; and/or (9) significantly inhibiting chemotaxis induced by biological fluids which contain multiple chemotactic factors including IL8.

Characterization of Binding of Human Monoclonal Antibodies to IL-8

To characterize binding of human monoclonal IL-8 antibodies of the invention, sera from immunized mice can be tested, for example, by ELISA. In a typical (but non-limiting) example of an ELISA protocol, microtiter plates are coated with purified IL-8 at 0.25 μg/mL in PBS, and then blocked with 5% bovine serum albumin (BSA) in PBS. Dilutions of plasma from IL-8-immunized mice are added to each well and incubated for 1-2 hours at 37° C. The plates are washed with PBS/Tween and then incubated with a goat-anti-human IgG Fc-specific polyclonal reagent conjugated to alkaline phosphatase for 1 hour at 37° C. After washing, the plates are developed with pNPP substrate (1 mg/mL), and analyzed at OD of 405-650. Preferably, mice which develop the highest titers will be used for fusions.

An ELISA assay as described above can also be used to screen for hybridomas that show positive reactivity with IL-8 immunogen. Hybridomas that bind with high avidity to IL-8 will be subcloned and further characterized. One clone from each hybridoma, which retains the reactivity of the parent cells (by ELISA), can be chosen for making a 5-10 vial cell bank stored at −140° C., and for antibody purification.

To purify human anti-IL-8 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected human anti-IL-8 monoclonal antibodies bind to unique epitopes, site-directed or multi-site directed mutagenesis can be used.

To determine the isotype of purified antibodies, isotype ELISAs can be performed. For example, wells of microtiter plates can be coated with 10 μg/mL of anti-human Ig overnight at 4° C. After blocking with 5% BSA, the plates are reacted with 10 μg/mL of monoclonal antibodies or purified isotype controls, at ambient temperature for two hours. The wells can then be reacted with either human IgG1 or human IgM-specific alkaline phosphatase-conjugated probes. Plates are developed and analyzed as described above.

Anti-IL-8 human IgGs can be tested for reactivity with IL-8 antigen by Western blotting. For example, cell extracts from cells producing IL-8 can be prepared and subjected to sodium dodecyl sulfate (SDS) polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

II. Production of Transgenic Non-Human Animals which Generate Human Monoclonal Anti-IL-8 Antibodies In yet another aspect, the invention provides transgenic and transchromosomal non-human animals, such as transgenic or transchromosomal mice, which are capable of expressing human antibodies that specifically bind to IL-8. In a particular embodiment, the invention provides a transgenic or transchromosomal mouse having a genome comprising a human heavy chain transgene, such that the mouse produces human anti-IL-8 antibodies when immunized with cells producing IL-8. The human heavy chain transgene can be integrated into the chromosomal DNA of the mouse, as is the case for transgenic, e.g., HuMAb mice, as described in detail herein and exemplified. Alternatively, the human heavy chain transgene can be maintained extrachromosomally, as is the case for transchromosomal (e.g., KM) mice. More particularly, in the KM mouse strain, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of WO 01/09187. This mouse strain carries a human kappa light chain transgene, KCoS, as described in Fishwild et al. (1996) *Nature Biotechnology* 14:845-851. This mouse strain also carries a human heavy chain transchromosome composed of chromosome 14 fragment hCF (SC20) as described in WO 02/43478.

Such transgenic and transchromosomal animals are capable of producing multiple isotypes of human monoclonal antibodies to IL-8 (e.g., IgG, IgA and/or IgE) by undergoing V-D-J/V-J recombination and isotype switching.

The design of a transgenic or transchromosomal non-human animal that responds to foreign antigen stimulation with a heterologous antibody repertoire, requires that the heterologous immunoglobulin transgenes contained within the transgenic animal function correctly throughout the pathway of B cell development. This includes, for example, isotype switching of the heterologous heavy chain transgene. Accordingly, transgenes are constructed so as that isotype switching can be induced and one or more of the following characteristics of antibody genes: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology*, 2nd edition (1989), Paul William E., ed. Raven Press, N.Y.

In certain embodiments, the transgenic or transchromosomal non-human animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res.* 15:7305-7316 (1991); Sideras et al., *Intl. Immunol.* 1:631-642 (1989)). For each of the foregoing transgenic animals, functionally rearranged heterologous heavy and light chain immunoglobulin transgenes are found in a significant fraction of the B cells of the transgenic animal (at least 10%).

The transgenes used to generate the transgenic non-human animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic animal when exposed to IL-8 antigen.

In an alternative embodiment, the transgenes comprise an unrearranged "minilocus". Such transgenes typically comprise a substantial portion of the C, D, and J segments as well as a subset of the V gene segments. In such transgene constructs, the various regulatory sequences, e.g., promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

Preferred transgenic and transchromosomal non-human animals, e.g., mice, will exhibit immunoglobulin production with a significant repertoire, ideally substantially similar to that of a human after adjusting for volume.

The repertoire will ideally approximate that shown in a human when adjusted for volume, usually with a diversity at least about 10% as great, preferably 25 to 50% or more. Generally, at least about a thousand different immunoglobulins (ideally IgG), preferably $10^4$ to $10^6$ or more, will be produced, depending on the number of different V, J and D regions introduced into the mouse genome and driven by the additional diversity generated by V(-D-)J gene segment rearrangements and random nucleotide additions at the joining regions. Typically, the immunoglobulins will exhibit an affinity ($K_D$) for preselected antigens of about $10^{-8}$ M or less, $10^{-9}$ M or less, or $10^{-10}$ M or even lower.

Transgenic and transchromosomal non-human animals, e.g., mice, as described above can be immunized with, for example, cells producing IL-8. Alternatively, the transgenic animals can be immunized with DNA encoding human IL-8. The animals will then produce B cells which undergo class-switching via switch recombination (cis-switching) and express immunoglobulins reactive with IL-8. The immunoglobulins will be human antibodies (also referred to as "human sequence antibodies"), wherein the heavy and light chain polypeptides are encoded by human transgene sequences, which may include sequences derived by somatic mutation and V region recombinatorial joints, as well as germline-encoded sequences; these human antibodies can be referred to as being substantially identical to a polypeptide sequence encoded by human $V_L$ and $J_L$ or $V_H$, $D_H$ and $J_H$ gene segments, even though other non-germline sequences may be present as a result of somatic mutation and differential V-J and V-D-J recombination joints. The variable regions of each antibody chain are typically at least 80% similar to human germline V, and J gene segments, and, in the case of heavy chains, human germline V, D, and J gene segments; frequently at least 85% similar to human germline sequences present on the transgene; often 90 or 95% or more similar to human germline sequences present on the transgene. However, since non-germline sequences are introduced by somatic mutation and VJ and VDJ joining, the human sequence antibodies will frequently have some variable region sequences which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

Another aspect of the invention includes B cells derived from transgenic or transchromosomal non-human animals as described herein. The B cells can be used to generate hybridomas expressing human monoclonal antibodies which bind with high affinity to human IL-8. Thus, in another embodiment, the invention provides a hybridoma which produces a human antibody having an affinity ($K_D$) of about $10^{-8}$ M or less, $10^{-9}$ M or less, $10^{-10}$ M or less when determined by surface plasmon resonance (SPR) technology in a BIACORE 3000 instrument using recombinant human IL-8 as the analyte and the antibody as the ligand, or when determined by scatchard analysis of IL-8 expressing cells using a radio-actively labeled monoclonal antibody, or by determination of the half-maximal binding concentration using FACS analysis.

Herein the monoclonal antibody comprises a human sequence light chain composed of (1) a light chain variable region having a polypeptide sequence which is substantially identical to a polypeptide sequence encoded by a human $V_L$ gene segment and a human $J_L$ segment, and (2) a light chain constant region encoded by a human $C_L$ gene segment; and a human sequence heavy chain composed of a (1) a heavy chain variable region having a polypeptide sequence which is substantially identical to a polypeptide sequence encoded by a human $V_H$ gene segment, a D region, and a human $J_H$ segment, and (2) a constant region encoded by a human $C_H$ gene segment.

The development of high affinity human monoclonal antibodies against IL-8 can be facilitated by a method for expanding the repertoire of human variable region gene segments in a transgenic non-human animal having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome (YAC) comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic animal produced by the V repertoire expansion method, wherein the animal expresses an immunoglobulin chain comprising a variable region sequence encoded by a V region gene segment present on the V region transgene and a C region encoded on the human Ig transgene. By means of the V repertoire expansion method, transgenic animals having at least 5 distinct V genes can be generated; as can animals containing at least about 24 V genes or more. Some V gene segments may be non-functional (e.g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a non-human animal germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast is no longer necessary (i.e., prior to introduction into a mouse ES cell or mouse prozygote). Methods of propagating the trait of human sequence immunoglobulin expression, include breeding a transgenic animal having the human Ig transgene(s), and optionally also having a functional YAC having an expanded V segment repertoire. Both $V_H$ and $V_L$ gene segments may be present on the YAC. The transgenic animal may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal of the invention, other embodiments are contemplated which have been classified in three categories:

I. Transgenic animals containing an unrearranged heavy and rearranged light chain immunoglobulin transgene;

II. Transgenic animals containing an unrearranged heavy and unrearranged light chain immunoglobulin transgene; and III. Transgenic animal containing rearranged heavy and an unrearranged light chain immunoglobulin transgene; Of these categories of transgenic animal, the preferred order of preference is as follows II>I>III where the endogenous light chain genes (or at least the κ gene) have been knocked out by homologous recombination (or other method) and I>II>III where the endogenous light chain genes have not been knocked out and must be dominated by allelic exclusion.

III. Pharmaceutical Compositions

In another aspect, the present invention provides a composition, e.g., a pharmaceutical composition, containing at least one human monoclonal antibody of the present invention, formulated together with a pharmaceutically acceptable carrier. In one embodiment, the composition includes a combination of multiple (e.g., two or more) isolated human antibodies of the invention. Preferably, each of the antibodies of the composition binds to a distinct, pre-selected epitope of IL-8.

Pharmaceutical compositions of the invention also can be administered in combination therapy, i.e., combined with other agents. For example, the combination therapy can include a composition of the present invention with at least one agent for treating inflammatory or hyperproliferative skin disorders, at least one anti-inflammatory agent, at least one immunosuppressive agent, or at least one chemotherapeutic agent.

In one embodiment, such therapeutic agents include one or more agents for inflammatory or hyperproliferative skin disorders, such as topical medications, including coal tar, A vitamin, anthralin, calcipotrien, tarazotene, and corticosteroids, oral or injected medications, such as corticosteroids, methotrexate, retinoids, e.g., acitretin, cyclosporine, etanercept, alefacept, efalizumab, 6-thioguanine, mycophenolate mofetil, tacrolimus (FK-506), and hydroxyurea. Other examples are CTLA4Ig and infliximab. Other treatments may include exposure to sunlight or phototherapy, including UVB (broad-band and narrow-band ultraviolet B), UVA (ultraviolet A) and PUVA (psoralen methoxalen plus ultraviolet A).

In a further embodiment, the compositions of the invention are administered in conjunction with two or more of the above therapies, such as methotrexate+phototherapy (PUVA or UVA); methotrexate+acitretin; acitretin+phototherapy (PUVA or UVA); methotrexate+acitretin+phototherapy (PUVA or UVB); hydroxyurea+phototherapy (PUVA or UVB); hydroxyurea+acitretin; cyclosporine+methotrexate; or calcipotrien+phototherapy (UVB).

In another embodiment such therapeutic agents include one or more anti-inflammatory agents, such as a steroidal drug or a NSAID (nonsteroidal anti-inflammatory drug). Preferred agents include, for example, aspirin and other salicylates, Cox-2 inhibitors, such as rofecoxib and celecoxib, NSAIDs such as ibuprofen, fenoprofen, naproxen, sulindac, diclofenac, piroxicam, ketoprofen, diflunisal, nabumetone, etodolac, oxaprozin, and indomethacin.

In another embodiment, such therapeutic agents include one or more DMARDs (disease modifying antirheumatic drugs), such as methotrexate, hydroxy-chloroquine, sulfasalazine, pyrimidine synthesis inhibitors, e.g., leflunomide, IL-1 receptor blocking agents, e.g., anakinra, and TNF-α blocking agents, e.g., etanercept, infliximab, and adalimumab. Further representatives are IL-10, anti-IL-15 antibodies, soluble IL-15R, and anti-CD20 antibodies.

In another embodiment, such therapeutic agents include one or more immunosuppressive agents, such as cyclosporine, azathioprine, mycophenolic acid, mycophenolate mofetil, corticosteroids, such as prednisone, methotrexate, gold salts, sulfasalazine, antimalarials, brequinar, leflunomide, mizoribine, 15-deoxyspergualine, 6-mercaptopurine, cyclophosphamide, rapamycin, and tacrolimus (FK-506).

In another embodiment, the compositions of the invention are administered in combination with two or more immunosuppressive agents, such as prednisone and cyclosporine; prednisone, cyclosporine and azathioprine; or prednisone, cyclosporine and mycophenolate mofetil.

In another embodiment, such therapeutic agents include one or more chemotherapeutics, such as doxorubicin, cisplatin, bleomycin, carmustin, cyclophosphamide, and chlorambucil.

In another embodiment, the present human monoclonal antibodies may be administered in conjunction with radiotherapy.

In another embodiment, the human antibodies of the invention may be administered in combination with one or more other antibodies, e.g., one or more human antibodies such as, e.g., anti-CD4 antibodies, anti-EGFr antibodies, anti-CD20 antibodies, anti-IL15 antibodies, or anti-IL15R antibodies.

In yet another embodiment, the human antibodies of the invention may be administered in combination with one or more agents, that block or interfere with the function of CC or CXC chemokine receptors, such as antibodies to CXCR1, CXCR2, CCR1, CCR2, or CCR5, or natural or synthetic molecules that act as chemokine receptor antagonists.

In still another embodiment, the human antibodies of the invention may be administered in combination with one or more agents, that block the function of chemokine ligands, such as antibodies to MIP-1α, MIP-1β, RANTES, MCP-1, MCP-2, MCP-3 or MCP-4.

Furthermore, the human anti-IL-8 antibodies of the present invention can be derivatized, linked to or co-expressed with other binding specificities. In a particular embodiment, the invention provides a bispecific or multispecific molecule comprising at least one first binding specificity for IL-8 (e.g., a human anti-IL-8 antibody or mimetic thereof), and a second binding specificity for a human effector cell, such as a binding specificity for an Fc receptor (e.g., a human Fcγ receptor, such as FcγRI, or a human Fcα receptor) or a T cell receptor, e.g., CD3.

Accordingly, the present invention includes bispecific and multispecific molecules that bind to both human IL-8 and to an Fc receptor or a T cell receptor, e.g., CD3. Examples of Fc receptors are, e.g., a human IgG receptor, e.g., an Fc-gamma receptor (FcγR), such as FcγRI (CD64), FcγRII (CD32), and FcγRIII (CD16). Other Fc receptors, such as human IgA receptors (e.g., FcαRT), also can be targeted. The Fc receptor is preferably located on the surface of an effector cell, e.g., a monocyte, macrophage or an activated mononuclear cell. In a preferred embodiment, the bispecific and multispecific molecules bind to an Fc receptor at a site which is distinct from the immunoglobulin Fc (e.g., IgG or IgA) binding site of the receptor. Therefore, the binding of the bispecific and multispecific molecules is not blocked by physiological levels of immunoglobulins.

As used herein, "pharmaceutically acceptable carrier" includes any and all solvents, dispersion media, coatings, antibacterial and antifungal agents, isotonicity and absorption delaying agents, and the like that are physiologically compatible. Preferably, the carrier is suitable for intravenous, intramuscular, subcutaneous, parenteral, spinal or epidermal administration (e.g., by injection or infusion).

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous acids and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release *Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonicity agents, for example, sugars, polyalcohols such as glycerol, mannitol, sorbitol, or sodium chloride in the composition. Prolonged absorption of the injectable compositions can be brought about by including in the composition an agent that delays absorption, for example, monostearate salts and gelatin.

In one embodiment the human monoclonal antibodies of the invention are administered in crystalline form by subcutaneous injection, cf. Yang et al. (2003) PNAS, 100(12): 6934-6939.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of 100%, this amount will range from about 0.01% to about 99% of active ingredient, preferably from about 0.1% to about 70%, most preferably from about 1% to about 30%.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection or infusion, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition). The dosage can be determined or adjusted by measuring the amount of circulating monoclonal anti-IL-8 antibodies at different time points following administration in a biological sample by making use of anti-idiotypic antibodies targeting the anti-IL-8 antibodies or by using other specific methods to detect the anti-IL8 antibodies for instance by an ELISA assay using IL-8 as coating.

In one embodiment, the human monoclonal antibodies according to the invention may be administered by infusion in a dosage of 0.15 to 8 mg/kg, e.g., 0.15 mg/kg, 0.5 mg/kg, 1.0 mg/kg, 1.5 mg/kg, 2.0 mg/kg, 4 mg/kg, or 8 mg/kg, on day 0 followed by 2 to 8 administrations once a week, such as 4 administrations once a week starting at day 28. The administration may be performed by continuous infusion over a period of 24 hours or over a period of more than 24 hours, in order to reduce toxic side effects.

In yet another embodiment, the human monoclonal antibodies are administered by maintenance therapy, such as, e.g., once a week, once every second week or once a month for a period of 6 months or more.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention can cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhancing targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res.* Commun. 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the desired area, e.g., the site of inflammation or infection, or the site of a tumor. The composition must be fluid to the extent that easy syringability exists. It must be stable under the conditions of manufacture and storage and must be preserved against the contaminating action of microorganisms such as bacteria and fungi.

The efficient dosages and the dosage regimens for the human monoclonal antibodies of the invention depend on the disease or condition to be treated and can be determined by the persons skilled in the art.

A "therapeutically effective dosage" for PPP preferably will result in a reduction in the overall PPP evaluation comparing impression of improvement after drug treatment with pretreatment condition. This can, e.g., be evaluated by the reduction in the number of fresh pustules, a PASI like score adapted to PPP denoted PPPASI. Preferably, the treatment will result in a PPPASI50, more preferably a PPPASI75, and even more preferably a PPPASI90.

A "therapeutically effective dosage" for psoriasis preferably will result in a PASI50, more preferably a PASI75, and even more preferably a PASI90 in the patients or a reduction in the overall psoriasis evaluation comparing impression of improvement after drug treatment with pretreatment condition. PASI (Psoriasis Area and Severity Index) is a score system used for evaluation of the area and severity of the disease. PASI50 is defined as ≥50% improvement of the score. In the same way, PASI75 and PASI90 are defined as ≥75% and ≥90% improvement of the score, respectively.

A "therapeutically effective dosage" for rheumatoid arthritis preferably will result in an ACR20 Preliminary Definition of Improvement in the patients, more preferred in an ACR50 Preliminary Definition of Improvement and even more preferred in an ACR70 Preliminary Definition of Improvement.

ACR20 Preliminary Definition of Improvement is defined as: ≥20% improvement in: Tender Joint Count (TJC) and Swollen Joint Count (SJC) and ≥20% improvement in 3 of following 5 assessments: Patient Pain Assessment (VAS), Patient Global assessment (VAS), Physician Global Assessment (VAS), Patient Self-Assessed Disability (HAQ), and Acute Phase Reactant (CRP or ESR).

ACR50 and ACR70 are defined in the same way with ≥50% and ≥70% improvements, respectively. For further details see Felson et al. in American College of Rheumatology Preliminary Definition of Improvement in Rheumatoid Arthritis; *Arthritis Rheumatism* (1995) 38:727-735.

Alternatively, a therapeutically effective dosage for rheumatoid arthritis can be measured by DAS (disease activity score), including DAS28 and more preferably DAS56, as defined by EULAR.

A "therapeutically effective dosage" for tumor therapy can be measured by objective tumor responses which can either be complete or partial. A complete response (CR) is defined as no clinical, radiological or other evidence of disease. A partial response (PR) results from a reduction in aggregate tumor size of greater than 50%. Median time to progression is a measure that characterizes the durability of the objective tumor response.

A "therapeutically effective dosage" for tumor therapy can also be measured by its ability to stabilize the progression of disease. The ability of a compound to inhibit cancer can be evaluated in an animal model system predictive of efficacy in human tumors. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

IV. Uses and Methods of the Invention

The human antibodies and antibody compositions of the present invention have numerous in vivo and in vitro therapeutic and diagnostic utilities involving the treatment and diagnosis of IL-8 mediated disorders or disorders involving IL-8 activity. These molecules can be administered to human subjects, e.g., in vivo, or to cells in culture, e.g., in vitro or ex vivo, to treat, prevent and to diagnose a variety of disorders. As used herein, the term "subject" is intended to include human and non-human animals). Preferred subjects include human patients having disorders caused by or associated with IL-8 activity.

More particularly, the human antibodies and derivatives thereof are used to inhibit IL-8 induced activities associated with certain disorders, e.g., proinflammatory activity, chemotactic activity, and angiogenesis. Other IL-8 induced activities which are inhibited by the antibodies of the present invention include inhibiting IL-8 induced increased expression of CD11b (Mac-1) and inhibiting IL-8 induced decreased expression of L-selectin. By contacting the antibody with IL-8 (e.g., by administering the antibody to a subject), the ability of IL-8 to bind to its receptors and to subsequently induce such activities is inhibited and, thus, the associated disorder is treated. Preferred antibodies bind to epitopes which are specific to IL-8 and, thus, advantageously inhibit IL-8 induced activities, but do not interfere with the activity of structurally related chemokines, such as GRO-α, GRO-β, IP-10 and NAP-2.

In one embodiment, the human antibodies of the invention can be used in methods for treating inflammatory or hyperproliferative skin disorders, such as PPP, psoriasis, including plaque psoriasis and guttate type psoriasis, bullous skin diseases, such as bullous pemphigoid, contact dermatitis, eczema, erythematosus, and atopic dermatitis.

In another embodiment, the human antibodies of the invention can be used in methods for treating immune, autoimmune, inflammatory or infectious diseases, such as psoriatic arthritis, systemic scleroderma and sclerosis, inflammatory bowel disease (IBD), Crohn's disease, ulcerative colitis, acute lung injury, such as acute respiratory distress syndrome or adult respiratory distress syndrome, meningitis, encephalitis, uveitis, multiple myeloma, glomerulonephritis, nephritis, asthma, atherosclerosis, leukocyte adhesion deficiency, multiple sclerosis, Raynaud's syndrome, Sjögren's syndrome, juvenile onset diabetes, Reiter's disease, Behcet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, lupus erythematosus, rheumatoid arthritis (RA), ankylosing spondylitis, pemphigus, Graves' disease, Hashimoto's thyroiditis, small vessel vasculitides, such as Wegener's granulomatosis, Omen's syndrome, chronic renal failure, autoimmune thyroid disease, acute infectious mononucleosis, HIV, herpes virus associated diseases, human virus infections, such as common cold as caused by human rhinovirus, coronavirus, other enterovirus, herpes virus, influenza virus, parainfluenza virus, respiratory syncytial virus or adenovirus infection, bacteria pneumonia, wounds, sepsis, cerebral stroke/cerebral edema, ischaemia-reperfusion injury and hepatitis C.

In one embodiment, the human monoclonal antibodies can be used for the treatment of ischaemia-reperfusion injury after thrombolysis, cardiopulmonary bypass, percutaneous coronary intervention (PCI), coronary artery bypass, or cardiac transplantation.

In yet another embodiment, the human antibodies of the invention can be used for treatment of alcoholic hepatitis and acute pancreatitis.

In yet a further embodiment, the human antibodies of the invention can be used in methods for treating diseases involving IL-8 mediated angiogenesis, such as tumors and cancers, e.g., melanoma, thyroid carcinoma, transitional cell carcinoma, trichilemmona, squamous cell carcinoma and breast cancer.

In another embodiment, the human antibodies of the invention can be used for treating diseases wherein blocking of granulocyte migration is beneficial, e.g., in diseases affecting the central nervous system, such as isolated cerebral angiitis;

diseases affecting the peripheral nervous system, such as mononeuritis multiplex;

cardiovascular disorders, such as acute myocardial infarction, myocarditis, pericarditis, and Liebman-Sachs endocarditis;

pulmonary disorders, such as chronic obstructive pulmonary disease (COPD), alveolitis, obliterating bronchiolitis, cystic fibrosis, allergic aspergillosis, and Löfflers syndrome;

hepatic disorders, such as sclerosing cholangiolitis;

urogenital disorders, such as chronic cyctitis;

renal disorders, such as tubulo-interstial nephritis;

infectious diseases, such as severe acute respiratory syndrome (SARS);

rheumatic disorders, such as large vessel vasculitides (including giant cell arteritis, polymyalgia rheumatica, and Takayasu arteritis), medium-sized vessel vasculitides (including polyarteritis *nodosa*, localized polyarteritis *nodosa*, and Kawasaki disease), small vessel vasculitides (including Churg-Strauss syndrome, microscopic polyarteritis, cryoglobulinemic vasculitis, and leucocytoclastic angiitis), secondary vasculitides (including rheumatoid vasculitis, and vasculitis associated with systemic lupus erythematosus or Sjögren's syndrome), isolated sacroileitis, the SAPHO syndrome, and disciitis (including postoperative disciitis);

endocrine disorders, such as subacute thyroiditis;

skin disorders, such as cicatricial pemphigoid, dermatitis herpetiformis, subcorneal pustular dermatosis, epidermolysis bullosa acquisita, rosacea, acute febrile dermatosis, granuloma annulare (including Sweet's syndrome), pyoderma gangraenosum, and acne (including acne conglobata);

connective tissue disorders, such as sarcoidosis, relapsing polychondritis, familial Mediterranean fever, panniculitis, erythema nodosum, Weber-Christian's disease, and retroperitoneal fibrosis.

In another embodiment, the human antibodies of the invention are used for treating diseases wherein interfering with interactions between IL-8 and osteoclasts is beneficial, such as osteoporosis, and osteolytic metastases.

In another embodiment, the human antibodies of the invention are used for treating disease wherein interfering with interactions between IL-8 and tumor cells is beneficial, such as gastric cancer, colorectal cancer, and urine bladder cancer.

The methods involve administering to a subject an antibody composition of the present invention in an amount effective to treat or prevent the disorder. The antibody composition can be administered alone or along with one or more further therapeutic agents, such as one or more agents selected from agents for treating inflammatory or hyperproliferative skin disorders, anti-inflammatory agents, immunosuppressive agents, and chemotherapeutic agents, which act in conjunction with or synergistically with the antibody composition to treat or prevent the IL-8 mediated disease.

Suitable routes of administering the antibody compositions of the invention in vivo and in vitro are well known in the art and can be selected by those of ordinary skill. For example, the antibody compositions can be administered by injection or infusion (e.g., intravenous or subcutaneous). Suitable dosages of the molecules used will depend on the age and weight of the subject, the concentration and/or formulation of the antibody composition, and the disease being treated.

As previously described, human anti-IL-8 antibodies of the invention can be co-administered with one or other more therapeutic agents. The antibody can be administered before, after or concurrently with the agent.

Also within the scope of the present invention are kits comprising the antibody compositions of the invention and instructions for use. The kit can further contain one ore more additional agents, such as an immunosuppressive agent, or one or more additional human antibodies of the invention (e.g., a human antibody having a complementary activity which binds to an epitope in the IL-8 antigen distinct from the first human antibody).

Accordingly, patients treated with antibody compositions of the invention can be additionally administered (prior to, simultaneously with, or following administration of a human antibody of the invention) with another therapeutic agent, such as an anti-inflammatory agent, which enhances or augments the therapeutic effect of the human antibodies.

In yet another embodiment, the invention provides methods for diagnosing diseases associated with IL-8 by detection ex vivo or in vitro of IL-8 in a sample, e.g., a tissue sample, a body fluid sample or a cell sample. This can be achieved, for example, by contacting a sample to be tested, optionally along with a control sample, with the human antibody under conditions that allow for formation of a complex between the antibody and IL-8. Complex formation can then be detected (e.g., using an ELISA). When using a control sample along with the test sample, complex can be detected in both samples and any statistically significant difference in the formation of complexes between the samples is indicative of the presence of IL-8 in the test sample.

The present invention is further illustrated by the following examples which should not be construed as further limiting.

EXAMPLES

Example 1 Production of Human Monoclonal Antibodies (HuMabs) Against IL-8

Human monoclonal antibodies against human IL-8 (72 amino acid form) were produced as follows in transgenic mice carrying human immunoglobulin transgenes.

Antigen:

Recombinant human IL-8 antigen (rhIL-8) was prepared using standard recombinant DNA techniques and provided at a protein concentration of 0.713 mg/mL in PBS. The soluble antigen was stored at −80° C. until use. Soluble IL-8 was mixed with Complete Freunds Adjuvant (CF) (Sigma F5881) for the first immunization. Thereafter, the antigen was mixed with Incomplete Freunds Adjuvant (IF) (Sigma F5506). Twenty-five micrograms of recombinant IL-8 in 100 µL PBS was mixed 1:1 with the adjuvant using an emulsifying needle. Mice were injected with 0.2 mL prepared antigen into the intraperitoneal cavity.

Transgenic Mice:

Mice were housed in filter cages and were evaluated to be in good physical condition on the dates of immunization and bleeds, and on the day of the fusion.

The mouse that produced monoclonal antibody (mAb) 10F8 was a male, ID #81645 of the (CMD)++; (HCo7) 19952+; (JKD)++; (KCoS) 9272+ genotype. Individual transgene designations are in parentheses, followed by line numbers for randomly integrated transgenes. The symbols ++ and + indicate homozygous or hemizygous. However, because the mice are routinely screened using a PCR-based assay that does not allow distinction between heterozygosity and homozygosity for the randomly integrated human Ig transgenes, a + designation may be given to mice that are actually homozygous for these elements.

The HCo7 mice have a JKD disruption in their endogenous light chain (kappa) genes (as described in Chen et al. (1993) *EMBO J.* 12: 821-830), a CMD disruption in their endogenous heavy chain genes (as described in Example 1 of WO 01/14424), a KCoS human kappa light chain transgene (as described in Fishwild et al. (1996) *Nature Biotechnology* 14:845-851), and a HCo7 human heavy chain transgene (as described in U.S. Pat. No. 5,770,429).

The HCo12 mice have a JKD disruption in their endogenous light chain (kappa) genes (as described in Chen et al. (1993) *EMBO J.* 12: 821-830), a CMD disruption in their endogenous heavy chain genes (as described in Example 1 of WO 01/14424 by Korman et al.), a KCoS human kappa light chain transgene (as described in Fishwild et al. (1996)

*Nature Biotechnology* 14:845-851), and a HCo12 human heavy chain transgene (as described in Example 2 of WO 01/14424 by Korman et al.).

Immunization Procedure:

The immunization schedule used for the mice is listed in Table 1 below. Splenocytes of ten mice from HCo7 and HCo12 genotypes immunized with rIL-8 were fused on Day 101.

TABLE 1

| Dates | Procedure |
| --- | --- |
| Day 0 | Immunization 25 µg IL-8 ip CF |
| Day 15 | Immunization 25 µg IL-8 ip IF |
| Day 28 | Immunization 25 µg IL-8 ip IF |
| Day 38 | Titer |
| Day 50 | Immunization 25 µg IL-8 ip IF |
| Day 59 | Titer |
| Day 63 | Immunization 25 µg IL-8 ip IF |
| Day 73 | Titer |
| Day −3 and −2 prior to fusion | Immunization 25 µug IL-8 iv |
| Day 101 | Fusion |

Hybridoma Preparation:

The P3 X63 ag8.653 myeloma cell line (ATCC CRL 1580, lot F-15183) was used for the fusions. The original ATCC vial was thawed and expanded in culture. A seed stock of frozen vials was prepared from this expansion. Cells were maintained in culture for 3-6 months, passed twice a week. P388D1 cell line (ATCC TIB-63 FL) was expanded to 200 mL and exhausted. The supernatant was spun down and filtered and used as a media addition known as conditioned media. This cell line was passed for 3-6 months and then a new vial was thawed.

High Glucose DMEM (Mediatech, Cellgro #10013245) containing 5% FBS, and Penicillin-Streptomycin (Cellgro #30004030) was used to culture the myeloma and P388D1 cells. Additional media supplements were added to the hybridoma growth media, which included: 3% Origen-Hybridoma Cloning Factor (Igen, 36335), 10% P388D1 conditioned media (8/10/99 DH), 10% FBS (Hyclone, SH30071 lot #AGH6843), L-glutamine (Gibco #1016483) 0.1% gentamycin (Gibco #1020070), 2-mercaptoethanol (Gibco #1019091), HAT ((Sigma, H0262) $1.0 \times 10^4$ M hypoxanthine, $4.0 \times 10^{-7}$ M aminopterin, $1.6 \times 10^{-5}$ M thymidine), or HT ((Sigma, H0137) $1.0 \times 10^{-4}$ M hypoxanthine, $1.6 \times 10^{-5}$ M thymidine).

The spleen from mouse #18645 was normal in size and yielded $1.8 \times 10^8$ viable cells. 10 (96-well) plates were dispensed at 200 µL/well. The splenocytes were then fused and an initial ELISA screen for human IgG,κ antibodies was performed 10-12 days post fusion.

Human IgG,κ positive wells were then screened on soluble IL-8 coated ELISA plates. Antigen positive hybridomas were then transferred to 24-well plates, and eventually to tissue culture flasks. IL-8 specific hybridomas were subcloned by limiting dilution to assure monoclonality. Antigen positive hybridomas were preserved at several stages in the development process by freezing cells in DMEM supplemented with 50% FBS plus 10% DMSO (Sigma, D2650).

The titers for mouse #18645 were as shown below in Table 2. The titers are Huγ antigen specific. Titer values are defined as the reciprocal of the highest dilution resulting in an OD equal to twice that of background.

TABLE 2

| Date | Titer |
| --- | --- |
| Day 0 | 200 |
| Day 21 | 1600 |
| Day 35 | 1600-3200 |

The fusion was screened for Huγ antigen reactivity by ELISA. Following the screen for antigen (ELISA based), two possible antigen specific hybridomas were identified from the fusion. These two hybridomas, along with six other hybridomas from prior fusions, were evaluated for therapeutic potential. These lines were subcloned and exhausted supernatants were purified over Protein-A. Determinations of $K_D$'s were done using BIAcore. When compared to the control mAb, hybridoma 10F8 was identified to have very high affinity and was selected for further characterization.

Example 2 Determination of the $V_H$ and $V_L$ Regions of the Antibodies

Cell Culture

HuMab 10F8 hybridoma cell line was cultured in Dulbecco's Modified Eagle Medium (DMEM, Gibco BRL) supplemented with 10% FCS, 2 mM L-glutamine, 100 IU/mL penicillin, 100 µg/mL streptomycin (pen/strep) (all derived from Gibco BRL, Life Technologies, Paisley, U.K.) and 1 mM sodium pyruvate. Cells were kept at 37° C. in a humidified atmosphere containing 5% $CO_2$.

RNA Preparation:

PolyA+ mRNA was prepared from $2 \times 10^6$ HuMab-IL-8 (10F8) cells using the Micro-Fast Track Kit (Invitrogen, Carlsbad, Calif., U.S.A.), following the manufacturer's protocol.

cDNA Preparation:

Complementary DNA (cDNA) of RNA from HuMab-IL-8 (10F8) cells was prepared from ¼ of the mRNA obtained, using the cDNA Cycle Kit (Invitrogen, Carlsbad, Calif., U.S.A.), following the manufacturer's protocol.

$V_H$ and $V_L$ regions were amplified using the following primers:

```
V_H FR1 5' primers:
AB62
                                    (SEQ ID NO: 25)
CAg gTK CAg CTg gTg CAg TC AB63
                                    (SEQ ID NO: 26)
SAg gTg CAg CTg KTg gAg TC AB65
                                    (SEQ ID NO: 27)
gAg gTg CAg CTg gTg CAg TC V_H leader 5' primers:
AB85
                                    (SEQ ID NO: 28)
ATg gAC Tgg ACC Tgg AgC ATC AB86
                                    (SEQ ID NO: 29)
ATg gAA TTg ggg CTg AgC Tg AB87
                                    (SEQ ID NO: 30)
ATg gAg TTT ggR CTg AgC Tg
```

```
AB88
                                              (SEQ ID NO: 31)
ATg AAA CAC CTg Tgg TTC TTC

AB89
                                              (SEQ ID NO: 32)
ATg ggg TCA ACC gCC ATC CT V_H 3' primer:
AB90
                                              (SEQ ID NO: 33)
TgC CAg ggg gAA gAC CgA Tgg V_K FR1 5' primers:
AB8
                                              (SEQ ID NO: 34)
RAC ATC CAg ATg AYC CAg TC AB9
                                              (SEQ ID NO: 35)
gYC ATC YRg ATg ACC CAg TC AB10
                                              (SEQ ID NO: 36)
gAT ATT gTg ATg ACC CAg AC AB11
                                              (SEQ ID NO: 37)
gAA ATT gTg TTg ACR CAg TC AB12
                                              (SEQ ID NO: 38)
gAA ATW gTR ATg ACA CAg TC AB13
                                              (SEQ ID NO: 39)
gAT gTT gTg ATg ACA CAG TC AB14
                                              (SEQ ID NO: 40)
gAA ATT gTg CTg ACT CAg TC V_K leader 5' primers:
AB123
                                              (SEQ ID NO: 41)
CCC gCT Cag CTC CTg ggg CTC CTg AB124
                                              (SEQ ID NO: 42)
CCC TgC TCA gCT CCT ggg gCT gC AB125
                                              (SEQ ID NO: 43)
CCC AgC gCA gCT TCT CTT CCT CCT gC AB126
                                              (SEQ ID NO: 44)
ATg gAA CCA Tgg AAg CCC CAg CAC AgC V_K 3' primer:
AB16
                                              (SEQ ID NO: 45)
Cgg gAA gAT gAA gAC AgA Tg
```

In the above primer sequences, K, S, R, Y and W have the following meanings:

K=G or T; S=C or G; R=A or G; Y=C or T; and W=A or T

PCR conditions used to amplify $V_H$ and $V_L$ regions for cloning: Polymerase chain reactions (PCR) were performed with cloned Pfu polymerase (Stratagene, La Jolla, Calif., U.S.A.) on a GeneAmp PCR System 9700 (Perkin Elmer Applied Biosystems, Foster City, Calif., USA).

| PCR cycling protocol: | |
|---|---|
| 10 cycles | 94° C. 2 min |
|  | 94° C. 45 sec |
|  | 65° C. 45 sec, minus 1° C. per cycle |
|  | 72° C. 1 min |
| 20 cycles | 94° C. 45 sec |
|  | 55° C. 45 sec |
|  | 72° C. 1 min |
|  | 72° C. 10 min |
|  | cool down to 4° C. |

Cloning of $V_H$ and $V_L$ in pCR-Blunt-Vector System:

After analysing the PCR products on an agarose gel, the products were ligated directly into the pCR-Blunt vector system (Invitrogen) according to the manufacturer's protocol. Three independently amplified $V_H$ PCR products, and five independently amplified $V_L$ PCR products, using FR1 or leader primers, were cloned and sequenced.

After transformation into *E. coli* TOP 10 (Invitrogen), plasmid DNA from colonies was purified using the Qiaprep Spin miniprep kit (Qiagen, Valencia, Calif., U.S.A). Individual clones were screened for $V_H$ or $V_L$ PCR product insert by digestion with EcoRI (New England Biolabs, Beverly, Mass., U.S.A.) and analysis on an agarose gel.

Sequencing:

The V-regions were sequenced after cloning in the pCR-Blunt Vector System, using T7 and T3 primers, by ACGT, Inc., Northbrook, Ill., U.S.A. The sequences were analysed with the program DNAStar, SeqmanII. The sequences were aligned to germline V-gene sequences in Vbase (See the website of the MRC Centre for Protein Engineering (Cambridge, UK), mrc-cpe.cam.ac.uk/imt-doc/public/intro.htm).

The germline family for the $V_H$-region of 10F8 according to alignment in Vbase: $V_H3$-33 ($V_H3$-subgroup), $J_H4$ (b) ($J_H$-segment). No complementary regions for $D_H$-segment could be recognized by V-base software, probably due to somatic hypermutations in the D-segment.

The germline family for the $V_L$-region of 10F8 according to alignment in Vbase: $V_K$ A-27 ($V_K$III-subgroup) and $J_K3$ ($J_K$-segment).

FIG. 1 shows the nucleotide sequences of the $V_L$ and $V_H$ regions of 10F8.

FIGS. 2 and 4 show the alignment of the 10F8 $V_L$ and $V_H$ region nucleotide sequences, respectively, with their corresponding germline sequences. FIGS. 3 and 5 show the alignment of the 10F8 $V_L$ and $V_H$ region amino acid sequences, respectively, with their corresponding germline-encoded sequences.

10F8: a human monoclonal IgG1,κ antibody with $V_H$ and $V_L$ amino acid sequences: SEQ ID NOs: 12 and 8, respectively.

Example 3 Expression of Recombinant HuMab 10F8

The cloned $V_L$ and $V_H$ regions from HuMab 10F8 were subcloned into the expression cassettes of an immunoglobulin expression vector. The V regions were inserted upstream of human kappa and gamma1 constant regions and encode full-length 10F8 heavy and light chains. The 10F8 expression vector was transfected into Chinese hamster ovary (CHO) cells and transfectoma cell lines expressing the recombinant antibody were established. The affinity of recombinant 10F8 produced from CHO cells was measured as being identical to the affinity of the hybridoma-derived 10F8 antibody as assessed by kinetic analyses of plasmon surface resonance using a BIAcore.

Example 4 Binding of HuMab 10F8 (Fab and IgG) to IL-8

Purification of monoclonal antibody from culture supernatant: HuMab 10F8 was purified by Protein-A affinity chromatography using the following procedure: (1) Loading Conditions: Supernatant was loaded on a 5 mL Protein-A column that was equilibrated with phosphate buffered saline (PBS); (2) Wash: PBS; (3) Elution: 0.1 M glycine with 150 mM NaCl, pH 2.9. The eluate was neutralized with 1M Tris buffer (30 µl for every 2 mL fraction). Each eluted fraction was run on gel before being pooled. Once the purity by coomassie staining was verified, fractions were pooled and dialyzed against 10 mM sodium phosphate buffer with 150 mM NaCl, pH 7.2.

Fab Fragment Preparation:

A Fab fragment preparation from HuMab 10F8 was performed according to kit instructions (Pierce Technical literature 44885). Five mg of the purified IgG was used for this purpose. The isolated Fab product was dialyzed against 10 mM sodium phosphate with 150 mM NaCl, pH 7.2 and its protein concentration was determined by BCA (Pierce) assay using BSA as a standard. The Fab was characterized for its purity and identity by SDS-PAGE.

Affinity Constants:

Affinity constants for 10F8 Fab were determined and compared with corresponding values of 10F8 IgG1,κ. Whole IgG molecules lead to rebinding effects during the dissociation phase of experimental procedures to determine the affinity, thus leading to an apparently lower dissociation rate constant and in turn, much higher affinity constant. To eliminate these artifactual avidity effects, Fab molecules were used in the place of IgG1,κ to determine the affinity and rate constants. A CM-5 chip was used to immobilize IL-8 via amine coupling.

Using a BIAcore 3000, the association and rate constants based on sensograms (data not shown) of IgG1,κ and Fab at 25° C. and 37° C. are summarized below.

| Association and rate constants @ 25° C. | | |
|---|---|---|
| | IgG | Fab |
| $k_a$ (×$10^5$/$M^{-1}$ × $sec^{-1}$) | 2.31 | 1.01 |
| $k_d$ (×$10^{-5}$ $sec^{-1}$) | 0.21 | 1.96 |
| $K_D$ (×$10^{-10}$M) | 0.1 | 1.94 |
| Half-life (ln (2/k_off hrs)) | 90.4 | 8.3 |

| Association and rate constants @ 37° C. | | |
|---|---|---|
| | IgG | Fab |
| $k_a$ (×$10^5$/$M^{-1}$ × $sec^{-1}$) | 2.75 | 1.06 |
| $k_d$ (×$10^{-5}$ $sec^{-1}$) | 0.54 | 3.94 |
| $K_D$ (×$10^{-10}$M) | 0.2 | 3.72 |
| Half-life (ln (2/k_off hrs)) | 38.2 | 4.9 |

Interaction of intact IgG1,κ with IL-8 yielded a dissociation rate constant of 0.21×$10^{-5}$ $sec^{-1}$, while the corresponding value for Fab was 1.96×$10^{-5}$ sec, indicating that rebinding and avidity effects influence the dissociation rate constant of IgG1,κ (yielding a higher affinity constant). These artifacts were eliminated with the use of Fab in the place of intact IgG1,κ.

Analysis of the interaction at the physiological temperature of 37° C., as compared to 25° C. (room temperature), showed that the rate constants are further affected, leading to relatively lower affinity constants, for both IgG1,k and Fab. The affinity constant of the Fab at 37° C. corresponds to the true affinity of each binding site at physiological temperature.

The half-life (i.e., the time taken for 50% of the complex to dissociate), was reduced by 50% at 37° C. This is an approximation of the actual biological half-life at physiological temperatures.

Unless otherwise stated, the hybridoma derived 10F8 antibody has been used in the following examples.

Example 5 Binding of HuMab 10F8 to Native IL-8 without Cross-Reacting with Other CXC Chemokines Possible cross-reactivity of HuMab 10F8 clone towards other chemokines was evaluated by ELISA. Briefly, microtiter ELISA plates (Greiner, Germany) were coated overnight at room temperature (RT) with 1 µg/mL of recombinant human (rh) GRO-α, rh-GRO-β, rh-IP-10, rh-IL-8 72 aa form, which is monocyte derived (IL-8M or IL-8Mpepretech) or rh-IL-8 77 aa form (IL-8E), which is endothelial cell derived, 100 µl per well. Plates were washed twice with PBST (phosphate buffered saline supplemented with 0.05% v/v Tween-20 (Fischer Scientific, USA)) and wells were blocked with 100 Owen PBSTC (PBST plus 2% v/v chicken serum) for 1 hour, RT. Thereafter, wells were incubated for 1 hour, RT under shaking conditions with HuMab-IL-8 clone 10F8, 20 µg/mL 1:3 diluted in PBSTC. Subsequently, wells were washed thrice with PBST and incubated with either HRP-conjugated rabbit anti-mouse IgG F(ab')$_2$ fragments (Jackson; diluted 1:3000 in PBSTC) or HRP-conjugated rabbit anti-human IgG F(ab')$_2$ (DAKO, Denmark; diluted 1:2000 in PBSTC) for the detection of mouse or human antibodies, respectively. Plates were washed thrice with PBST and assays were developed with freshly prepared ABTS solution (1 mg/mL) (ABTS: 2,2'-azino bis (3-ethyl-benzthiazoline-6-sulfonic acid; 2 tablets of 5 mg in 10 mL ABTS buffer, Boehringer Mannheim, Germany) for 30 minutes at RT in the dark. Absorbance was measured at 405 nm in an ELISA plate reader (Biotek Instruments Inc., Winochi, USA). The results shown in FIG. 6 are representative out of three experiments performed. As it appears HuMab 10F8 binds to both endothelial cell derived human IL-8 and to monocyte derived human IL-8. However, it does not cross-react with the chemokines GRO-α, GRO-β or IP-10.

Example 6 Inhibition of IL-8 Binding to IL-8R on Neutrophils

Figure 7A:
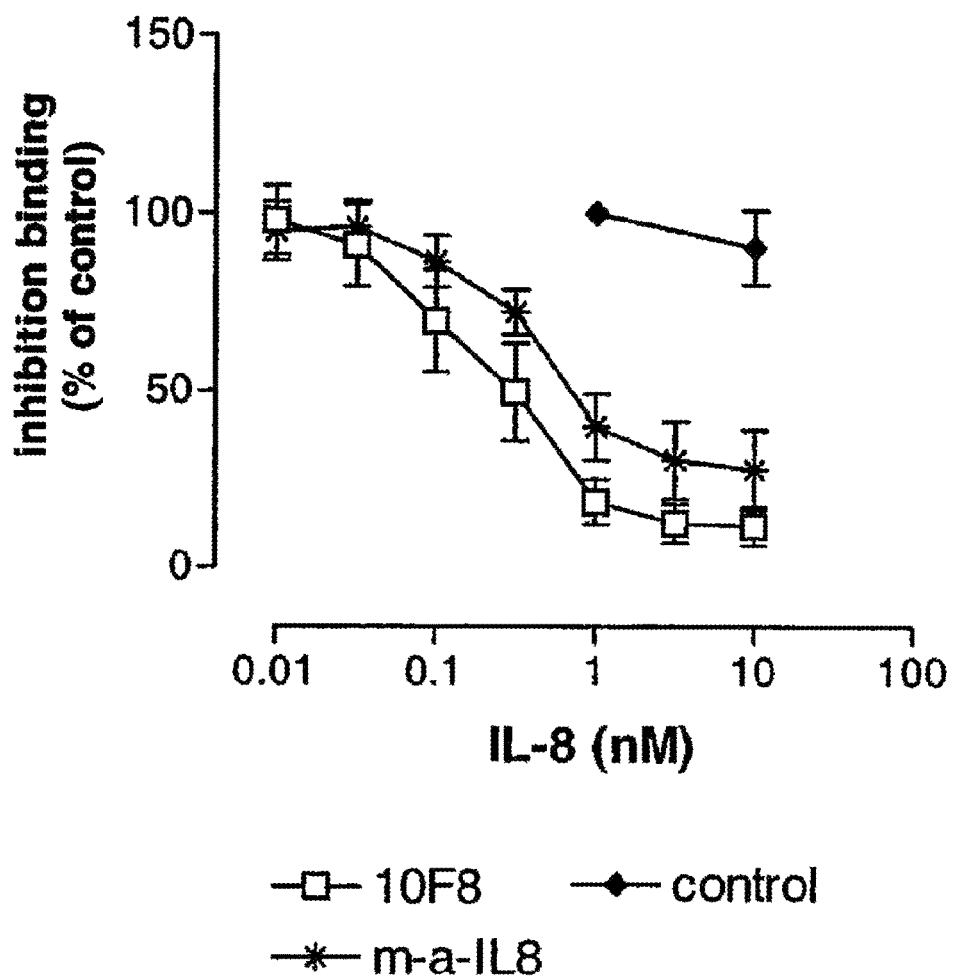
FIG. 7A is a graph showing inhibition of [$^{125}$I]-IL-8 binding to neutrophils by HuMab 10F8 (open squares) as compared to a murine IL-8-specific antibody (m-a-IL8) (asterisks).
Figure 7B:
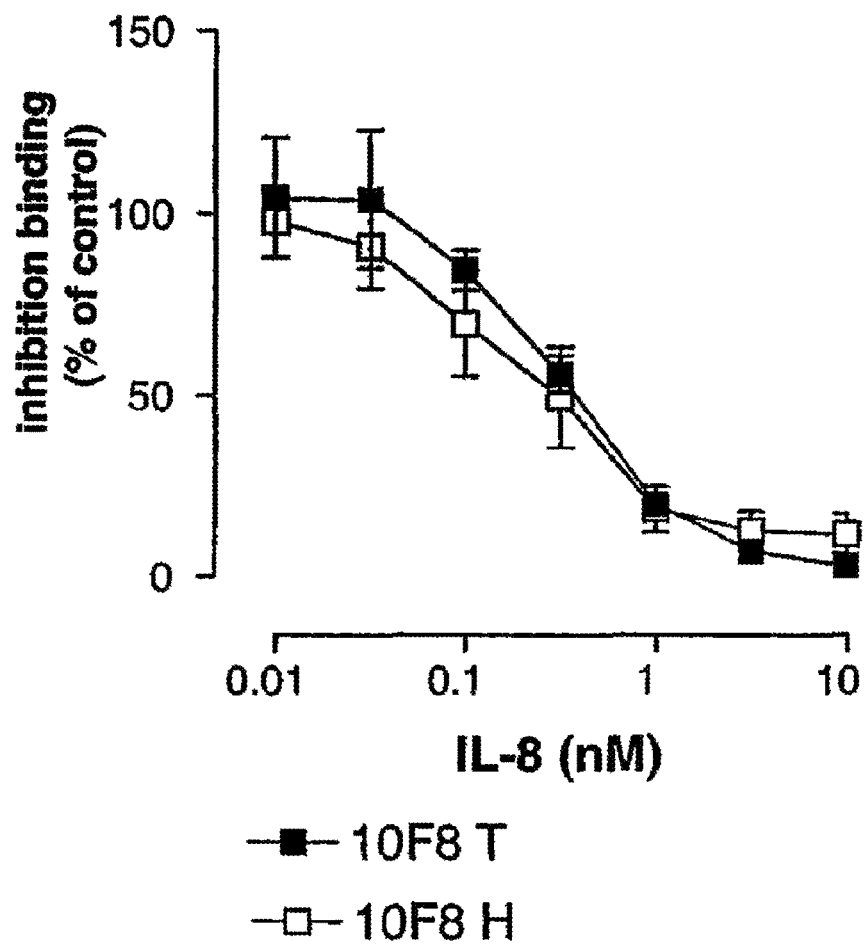
FIG. 7B is a graph showing inhibition of [$^{125}$I]-M-8 binding to neutrophils by hybridoma-derived HuMab 10F8 (10F8 H) (open squares) and transfectoma-derived HuMab 10F8 (10F8 T) (closed squares), respectively.

The ability of HuMab 10F8 to inhibit radiolabeled IL-8 binding to IL-8 receptors (CXCR1 and CXCR2) on neutrophils was assessed as follows:

Neutrophils were enriched from heparinized whole blood from normal volunteers. The blood was layered on Ficoll-hypaque and centrifuged at 1500 rpm for 30 minutes. The mononuclear cell layer was removed, and erythrocytes were hypotonically lysed. The resulting neutrophils were resuspended in PBS containing 0.1% BSA and 0.02% Na azide (0.1% PBA) and held on ice. The IL-8 binding assay was performed as previously described (Yang et al, (1999) J. Leukoc. Biol. 66:401-410). Briefly, in a final volume of 150 µl, 4×$10^5$ neutrophils were incubated from 1.5-3 hours on ice with 0.25 nM [$^{125}$I] recombinant human IL-8 (Amersham Life Sciences, Piscataway, N.J.) along with varying concentrations of 10F8 (hybridoma-derived), 10F8 (transfectoma-derived), mouse anti-human IL-8 mAb 6712.111 R & D Systems, and control antibody. All incubations were performed in 96 well Multiscreen filter plates (Millipore, Bedford, Mass.). Plates were washed extensively with cold 0.1% PBA, and filters were counted on a Wallac gamma counter. Results are shown in FIGS. 7A and 7B, expressed as means of triplicate or quadruplicates. The inhibition of binding is expressed as percentage of control antibody.

As shown in FIGS. 7A and 7B, HuMab 10F8 inhibited the binding of labeled IL-8 to neutrophils in a dose-dependent fashion. The murine anti-IL-8 antibody also was able to inhibit binding of labeled IL-8 to neutrophils in a dose-dependent fashion, but 10F8 was consistently more potent than the murine antibody in inhibiting IL-8 binding to neutrophils. In the experiment shown in FIG. 7B, the $IC_{50}s$ of 10F8 (hybridoma-derived) (10F8 H) and 10F8 (transfectoma-derived) (10F8 T) were 0.19 nM and 0.30 nM, respectively.

Overall, the foregoing results demonstrate that HuMab 10F8 inhibits the binding of IL-8 to its receptors in a dose-dependent fashion, and is able to inhibit this binding at lower concentrations than a commercially available murine anti-IL-8 antibody.

Example 7 Inhibition of IL-8 Mediated Neutrophil Chemotaxis

The ability of HuMab 10F8 and a murine anti-IL-8 antibody (MAb 6217.111, R & D Systems) to inhibit IL-8 induced neutrophil migration was evaluated utilizing a chemotaxis assay.

Neutrophils were incubated in one chamber of a transwell plate. IL-8 (rhIL-8) was incubated with varying concentrations of HuMab 10F8, the murine anti-IL-8 MAb, and a control antibody in the other chamber of the transwell plate. The assay was incubated at 37° C. for two hours, and cell migration was quantified.

Figure 8A:
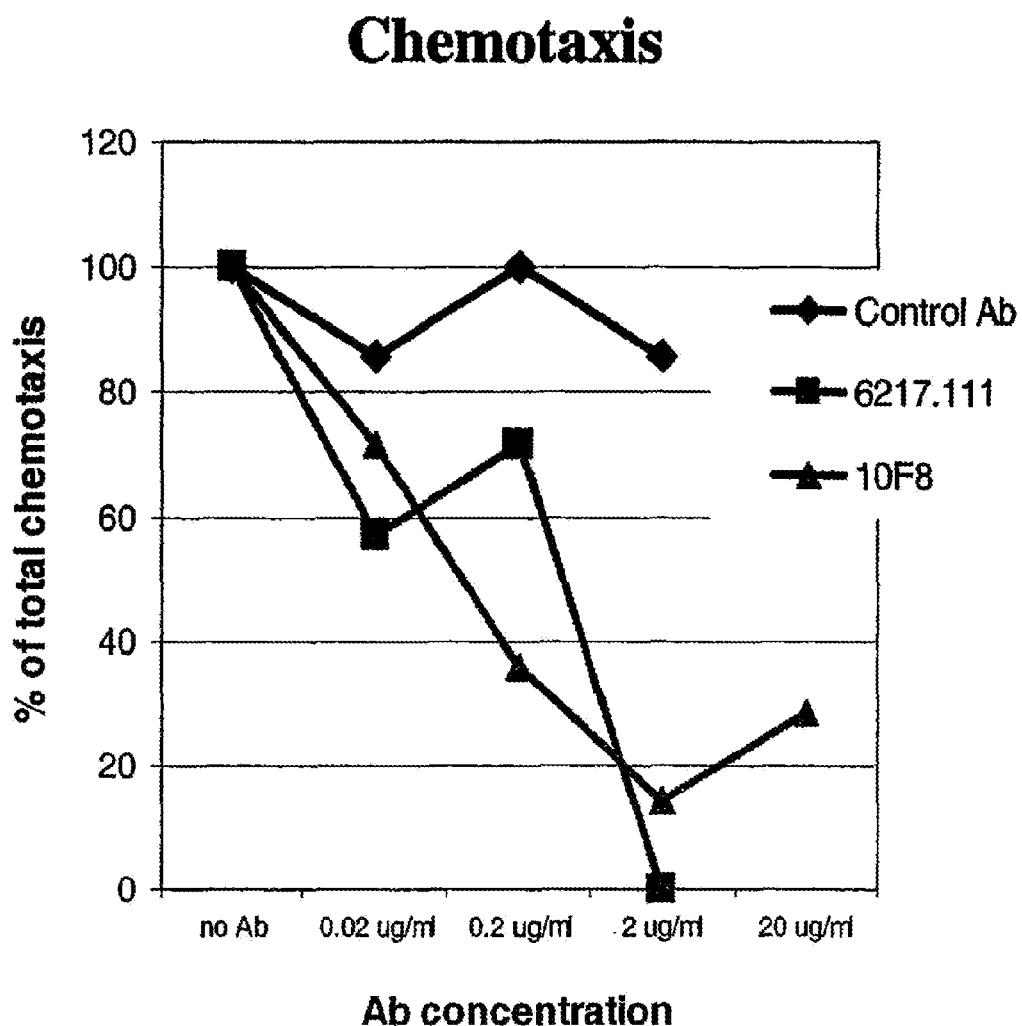
FIG. 8A is a graph showing inhibition of IL-8 mediated neutrophil chemotaxis by HuMab 10F8 (triangles) as compared to a murine IL-8-specific antibody (6217.111) (squares).

The data depicted in FIG. 8A show that neutrophil chemotaxis was inhibited in a dose-dependent manner by HuMab 10F8 and also by the murine IL-8-specific antibody. The control antibody did not inhibit chemotaxis. These data demonstrate that HuMab 10F8 can inhibit neutrophil migration, an important function of IL-8 in vivo.

The ability of HuMab 10F8 to inhibit transmigration of human neutrophils towards human IL-8 was furthermore studied utilizing a Boyden chamber.

Human IL-8 ($10^{-8}$M) was incubated with varying concentrations of HuMab 10F8 in the lower compartment of the Boyden chamber. Neutrophils ($4 \times 10^5$ cells) were incubated in the upper compartment. The assay was incubated at 37° C. for 1 hour, and cell migration was quantified.

Figure 8B:
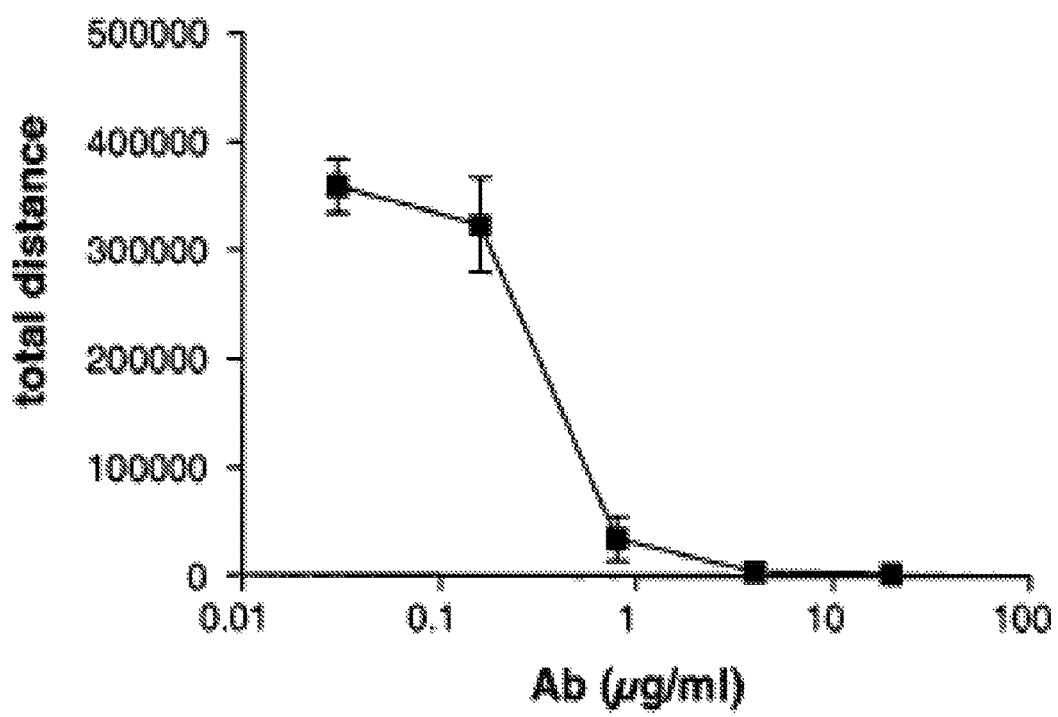
FIG. 8B is a graph showing inhibition of IL-8 mediated neutrophil chemotaxis by HuMab 10F8 as determined by a transmigration assay using a Boyden chamber.

The data depicted in FIG. 8B show that neutrophil chemotaxis was inhibited in a dose-dependent manner by HuMab 10F8. These data also demonstrate that HuMab 10F8 can inhibit neutrophil migration, an important function of IL-8 in vivo.

Example 8 Change of IL-8 Induced Adhesion Molecule Expression on Neutrophils

Human neutrophils show increased expression of CD11b (Mac-1) and decreased expression of L-selectin (CD62L) when stimulated with IL-8. The capacity of 10F8 to inhibit the IL-8 induced changes in expression of adhesion molecules on PMN was studied by flow cytometry. Briefly, 100 µl of 1:5 diluted whole blood was incubated with serial dilutions of 10F8 (5, 2.5, 1.25, 0.625, 0.312, 0 µg/mL) in the absence or presence of 25 ng/mL recombinant human IL-8 (rh-IL-8, 72 aa, Peprotech) in 96-well flat bottomed culture plates, to a final volume of 200 µl per well, for 2 hours at 37° C. and 5% $CO_2$. Thereafter, cells were spun down and the supernatant was stored at −20° C. until further assessment for the presence of lactoferrin. Cells were replenished with 200 µl cold FACS buffer (PBS, supplemented with 0.02% (v/v) azide and 0.1% (w/v) BSA) and washed twice with 200 µl cold FACS buffer. Cells were spun down and incubated with 1.5 mg/mL PE-conjugated mouse anti-human CD11b (Becton Dickinson) and 1.5 mg/mL FITC-conjugated mouse anti-human CD62L (Becton Dickinson) to a final volume of 20 µl per well, for 30 minutes at 4° C. in the dark. Thereafter, erythrocytes were lysed with FACSlysis buffer according to the manufacturers protocol (FACSlysing solution kit, Becton Dickinson, cat#349202). Subsequently, cells were washed with cold FACS buffer. Fluorescence intensity of cells was analyzed by flow cytometry (FACS Calibur, Becton Dickinson) using Cell Quest software.

Figure 9A:
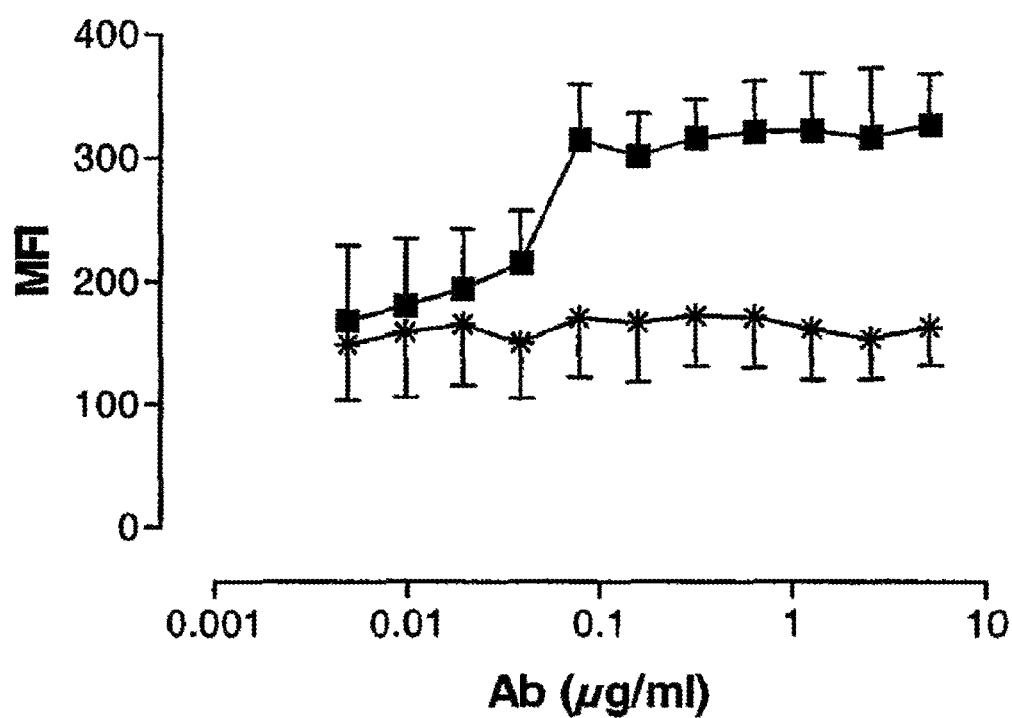
FIG. 9A is a graph showing inhibition of IL-8 mediated shedding of L-selectin (CD62L) on the surface of neutrophils by HuMab 10F8 (closed squares) as compared to an irrelevant human isotype control antibody (asterisks).
Figure 9B:
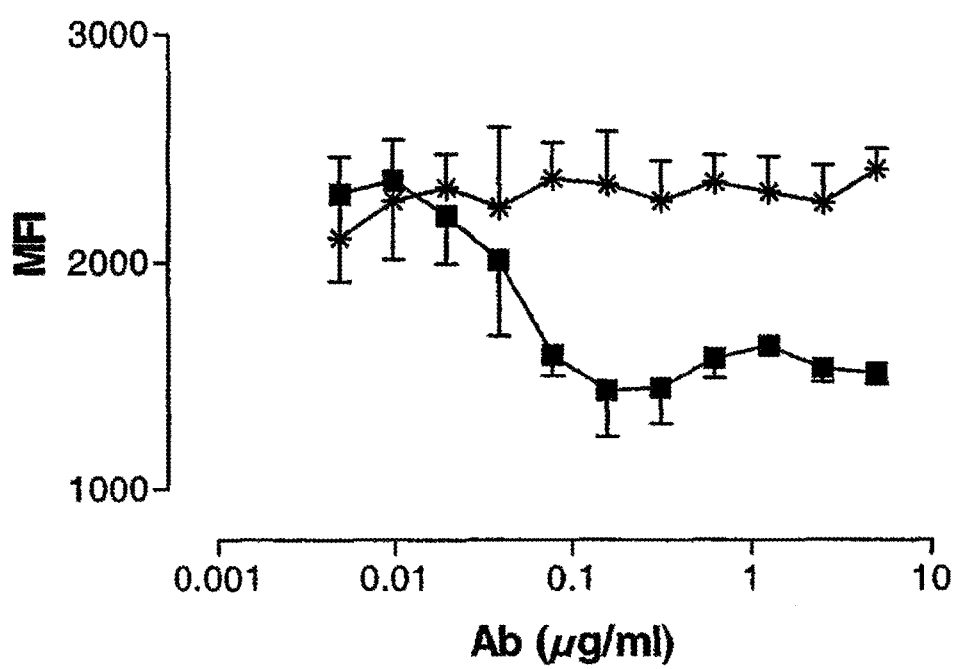
FIG. 9B is a graph showing inhibition of IL-8 mediated expression of CD11b on the cell surface of neutrophils by HuMab 10F8 (closed squares) as compared to an irrelevant human isotype control antibody (asterisks).

Stimulation of PMN with IL-8 resulted in an altered expression of adhesion molecules, e.g., an enhanced expression of CD11b and a decreased expression of CD62L due to shedding of the molecule. The mean baseline expression of CD11b on PMN was 1538±37 (n=3) MFI (Mean Fluorescence Intensity, a measurement for the number of molecules per cell) and the expression of CD11b was up-regulated to 2341±274 units after stimulation of cells with 25 ng/mL IL-8. Baseline expression of CD62L was 274±24 (n=3) MFI and the expression of CD62L was down regulated to 176±60 units after addition of 25 ng/mL IL-8. In the present study, it was demonstrated that 10F8 is capable of inhibiting these IL-8 induced changes in expression of cell surface molecules. The cell surface expression of CD11b, as well as CD62L, was measured by flow cytometry after stimulation of cells with 25 ng/mL IL-8 alone or in the presence of 10F8 or an irrelevant control antibody. FIG. 9A shows the expression of CD62L on IL-8 stimulated PMN. In the presence of an irrelevant isotype control antibody (asterisks), the MFI on these stimulated PMN fluctuated around 150, indicating that this antibody does not block IL-8 mediated PMN activation. However, when cells were stimulated with IL-8 in the presence of increasing concentrations of 10F8 (closed squares), reduced IL-8 mediated CD62L shedding was observed, in a dose-dependent way indicative for an inhibition of IL-8 induced cell activation by 10F8. Consistent with this, 10F8 (closed squares) reduced IL-8-mediated CD11b up-regulation, whereas an irrelevant isotype control antibody (asterisks) failed to show an effect, i.e., the expression level of CD11b remained unaffected (MFI around 2400) (n=3; FIG. 9B). Increasing concentrations of 10F8 were correlated with lesser expression of CD11b, clearly demonstrating an inhibitory effect of 10F8 on PMN activation by IL-8.

In summary, the results shown in FIGS. 9A and 9B demonstrate that HuMab 10F8 is capable of inhibiting: a) the increased expression of CD11b on neutrophils that is mediated by IL-8; b) the shedding of L-selectin (CD62L) on the surface of neutrophils that is mediated by IL-8.

Example 9 IL-8 Present in Pustulosis Palmoplantaris (PPP) Material

Sterile material was obtained from blisters of PPP patients (ppp blister), eczema patients or healthy volunteers. In addition patients and healthy controls provided test material by wrapping the feet or hands in foil containing 2 mL phosphate buffered saline (PBS). The wrapped feet or hands were placed in a 37° C. water bath to facilitate diffusion of blister content into the PBS (ppp water bath). Blister materials or water bath materials were analysed for the presence of CXC chemokines or complement factor C5a by commercial available ELISAs (IL-8: Pelikine Compact™, CLB, Amsterdam, The Netherlands; or IL-8: Quantikine® Human IL-8 kit, R&D kit; GRO-α: Quantikine® Human GRO-α kit, R&D Systems; ENA-78: Quantikine® ENA-78 kit, R&D Systems; C5a kit, Opteia, BD-Pharmingen). Normal human serum was used as negative control. ELISAs were performed according to the manufacturer's protocols.

Figure 10:
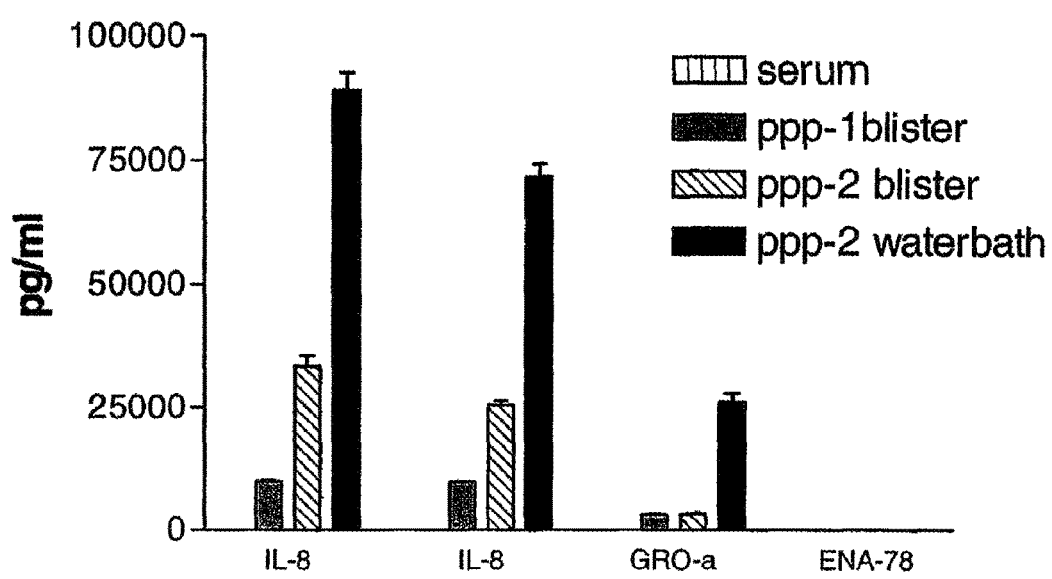
FIG. 10 is a graph showing the presence of IL-8 and GRO-α in pustulosis palmoplantaris (PPP) patient material as determined by ELISAs.

The data depicted in FIG. 10 show that IL-8 is present in patient material obtained from blisters and the water bath material, whereas IL-8 could not be demonstrated in normal serum from a healthy volunteer. IL-8 was measured on two separate occasions and it was demonstrated that the IL-8 content in the patient material did not decrease in time. GRO-α was also present in the patient materials, albeit to a lesser extent. The CXC chemokine ENA-78 could not be demonstrated in any of the obtained materials.

Table 3 shows that IL-8 is present in PPP patients, whereas IL-8 was undetectable in water bath material obtained from an eczema patient or healthy control. GRO-α was also present in PPP patient material, albeit to a lesser extent. The samples were measured on 3 separate occasions and demonstrated that the IL-8 or GRO-α content in the patient material did not decrease in time and was not degraded by presence of proteases.

TABLE 3

| Sample No. | IL-8 | | | GRO-a | | |
|---|---|---|---|---|---|---|
| | µg/ml | SEM | n | µg/ml | SEM | n |
| No. 1 - Fluid from pustules (ppp) | 17 | 3 | 3 | 2 | 0 | 1 |
| No. 2 - Fluid from pustules (ppp) | 517 | 213 | 3 | 39 | 8 | 2 |
| No. 3 - Foot wash fluid (ppp) | 52 | 2 | 3 | 21 | 4 | 2 |
| No. 4 - Foot wash fluid (ppp) | 15 | 3 | 3 | 42 | 6 | 2 |
| No. 5 - Foot wah fluid (ppp) | 15 | 4 | 3 | 45 | 1 | 2 |

TABLE 3-continued

| Sample No. | IL-8 | | | GRO-a | | |
|---|---|---|---|---|---|---|
| | µg/ml | SEM | n | µg/ml | SEM | n |
| No. 6 - Hand wash fluid (eczema) | 0 | 0 | 3 | 0 | 0 | 2 |
| No. 7 - Hand wash fluid (control) | 0 | 0 | 3 | 0 | 0 | 2 |
| No. 8 - Fluid from pustules (ppp) | 32 | 16 | 2 | 2 | 0 | 1 |
| No. 9 - Foot wash fluid (ppp) | 45 | 13 | 2 | 32 | 13 | 3 |

Figure 11:
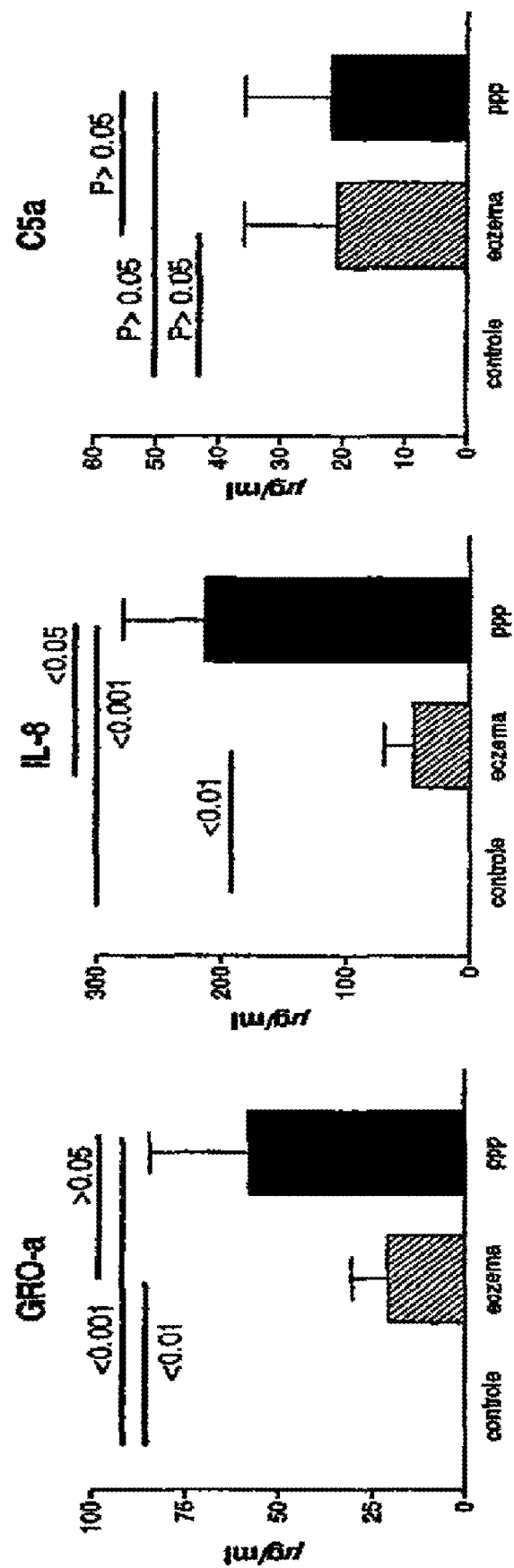
FIG. 11 shows the results of the measurement of IL-8, GRO-α and C5a present in feet water fluid obtained from healthy controls (n=6), eczema patients (n=6) or PPP patients (n=6).

FIG. 11 shows the results of the measurement of chemokines present in feet water fluid obtained from healthy controls (n=6), eczema patients (n=6) or PPP patients (n=6). Analysis was performed on log transformed data by one-way ANOVA with Tukey test. $P<0.05$ was considered significantly different.

Both eczema and PPP patients show significant increase of IL-8 and GRO-α as compared to the healthy controls. Comparison of the eczema and PPP patients shows that the amount of IL-8 is significantly different between eczema and PPP patients ($P<0.05$), whereas the amount of GRO-α is not significantly different between the two groups ($P>0.05$). Furthermore, the amount of C5a was measured and although some samples showed an increased amount of C5a (present in both PPP and eczema groups), no significant differences with the control group could be observed.

These data underline the presence of IL-8 in material obtained from PPP patients and provide a rationale for using an anti-IL-8 antibody as a therapeutic agent in this disease.

EQUIVALENTS

Those skilled in the art will recognize, or be able to ascertain using no more than routine experimentation, many equivalents of the specific embodiments of the invention described herein. Such equivalents are intended to be encompassed by the following claims. Any combination of the embodiments disclosed in the dependent claims are also contemplated to be within the scope of the invention.

INCORPORATION BY REFERENCE

All patents, pending patent applications and other publications cited herein are hereby incorporated by reference in their entirety.

We claim:

1. An isolated recombinant monoclonal antibody which binds to human IL-8 comprising a variable heavy chain amino acid sequence as set forth in SEQ ID NO:12 and a variable light chain amino acid sequence as set forth in SEQ ID NO:8.

2. An isolated recombinant monoclonal antibody which binds to human IL-8, wherein the antibody comprises a human heavy chain variable region comprising CDR1, CDR2, and CDR3 sequences comprising the amino acid sequences set forth in SEQ ID NOs:22, 23, and 24, respectively, and a human light chain variable region comprising CDR1, CDR2, and CDR3 sequences comprising the amino acid sequences set forth in SEQ ID NOs:16, 17 and 18, respectively.

3. The antibody of claim 2, wherein the antibody is an IgG1 antibody.

4. The antibody of claim 3, wherein the antibody is an IgG1κ or IgG1λ, isotype.

5. The antibody of claim 3, comprising an IgG1 or IgG3 heavy chain.

6. The antibody of claim 2, wherein the antibody has one or more of the following characteristics: (i) inhibits IL-8 binding to its receptors (CXCR1 and CXCR2); (ii) inhibits IL-8 induced proinflanimatory effects; (iii) inhibits IL-8 induced chemotactic activity for neutrophils; (iv) inhibits IL-8 induced calcium flux; (v) inhibits IL-8 induced changes in expression levels of adhesion molecules on neutrophils; (vi) inhibits IL-8 induced increased expression of CD11b (Mac-1) and inhibits IL-8 induced decreased expression of L-selectin on neutrophils; or (vii) does not cross-react with related chemokines selected from the group consisting of human GRO-alpha, human GRO-beta, human IP-10 and human NAP-2.

7. The antibody of claim 2 having a dissociation equilibrium constant (KD) of approximately $10^{-8}$ M or less, when determined by surface plasmon resonance (SPR) technology using recombinant human IL-8 as the analyte and the antibody as the ligand.

8. The antibody of claim 2 which is an antibody fragment or a single chain antibody.

9. The antibody of claim 2 which is a binding-domain immunoglobulin fusion protein comprising (i) a variable heavy chain amino acid sequence as set forth in SEQ ID NO:12, fused to a variable light chain amino acid sequence as set forth in SEQ ID NO:8 via a linker peptide, that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region.

10. The antibody of claim 2, produced by a hybridoma which includes a B cell obtained from a transgenic non-human animal, in which V-(D)-J gene segment rearrangements have resulted in the formation of a functional human heavy chain transgene and a functional human light chain transgene, fused to an immortalized cell.

11. A bispecific or multispecific molecule comprising the antibody according to claim 2, and a binding specificity for a human effector cell.

12. The molecule of claim 11, wherein the binding specificity for a human effector cell is selected from the group consisting of a binding specificity for a human Fc gamma receptor, a human Fc alpha receptor, and a T cell receptor.

13. A composition comprising the antibody of claim 2 and a pharmaceutically acceptable carrier.

14. The composition of claim 13, comprising at least one therapeutic agent.

15. The composition of claim 14, wherein the agent is selected from the group consisting of agents for treating inflammatory or hyperproliferative skin disorders, and anti-inflammatory agents.

* * * * *

SEQUENCE LISTING

```
<160> NUMBER OF SEQ ID NOS: 47

<210> SEQ ID NO 1
<211> LENGTH: 381
<212> TYPE: DNA
<213> ORGANISM: Homo sapiens
<220> FEATURE:
<221> NAME/KEY: CDS
<222> LOCATION: (1)...(381)

<400> SEQUENCE: 1 atg gaa acc cca gcg cag ctt ctc ttc ctc ctg cta ctc tgg ctc cca         48
Met Glu Thr Pro Ala Gln Leu Leu Phe Leu Leu Leu Leu Trp Leu Pro
 1               5                  10                  15 gat acc acc gga gaa att gtg ttg acg cag tct cca ggc acc ctg tct         96
Asp Thr Thr Gly Glu Ile Val Leu Thr Gln Ser Pro Gly Thr Leu Ser
             20                  25                  30 ttg tct cca ggg gaa aga gcc acc ctc tcc tgc agg gcc agt cag agt        144
Leu Ser Pro Gly Glu Arg Ala Thr Leu Ser Cys Arg Ala Ser Gln Ser
         35                  40                  45
```

```
att agc agc agc tac tta gcc tgg tac cag cag aaa cct ggc cag gct      192
Ile Ser Ser Ser Tyr Leu Ala Trp Tyr Gln Gln Lys Pro Gly Gln Ala
    50                  55                  60 ccc agg ctc ctc atc tat ggt cca tcc agc agg gcc act ggc atc cca      240
Pro Arg Leu Leu Ile Tyr Gly Pro Ser Ser Arg Ala Thr Gly Ile Pro
65                  70                  75                  80 gac agg ttc agt ggc agt ggg tct ggg aca gac ttc act ctc acc atc      288
Asp Arg Phe Ser Gly Ser Gly Ser Gly Thr Asp Phe Thr Leu Thr Ile
                85                  90                  95 agc aga ctg gag cct gaa gat ttt gca gtg tat tac tgt cag cag tat      336
Ser Arg Leu Glu Pro Glu Asp Phe Ala Val Tyr Tyr Cys Gln Gln Tyr
            100                 105                 110 gct ggc tca ctc act ttc ggc cct ggg acc aaa gtg gat atc aaa          381
Ala Gly Ser Leu Thr Phe Gly Pro Gly Thr Lys Val Asp Ile Lys
        115                 120                 125

<210> SEQ ID NO 2
<211> LENGTH: 127
<212> TYPE: PRT
<213> ORGANISM: Homo sapiens

<400> SEQUENCE: 2

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Ile Ser Ser Ser Tyr Leu Ala Trp Tyr Gln Gln Lys Pro Gly Gln Ala
    50                  55                  60

Pro Arg Leu Leu Ile Tyr Gly Pro Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Ala Gly Ser Leu Thr Phe Gly Pro Gly Thr Lys Val Asp Ile Lys
        115                 120                 125

<210> SEQ ID NO 3
<211> LENGTH: 408
<212> TYPE: DNA
<213> ORGANISM: Homo sapiens
<220> FEATURE:
<221> NAME/KEY: CDS
<222> LOCATION: (1)...(408)

<400> SEQUENCE: 3 atg gag ttt ggg ctg agc tgg gtt ttc ctc gtt gct ctt tta aga ggt      48
Met Glu Phe Gly Leu Ser Trp Val Phe Leu Val Ala Leu Leu Arg Gly
1               5                   10                  15 gtc cag tgt cag gtg caa ctg gtg gag tct ggg gga ggc gtg gtc cag      96
Val Gln Cys Gln Val Gln Leu Val Glu Ser Gly Gly Gly Val Val Gln
            20                  25                  30 cct ggg agg tcc ctg aga ctc tcc tgt aca gcg tct gga ttc acc ttc      144
Pro Gly Arg Ser Leu Arg Leu Ser Cys Thr Ala Ser Gly Phe Thr Phe
        35                  40                  45 agt cac tat ggc atg tac tgg gtc cgc cag gct cca ggc aag ggg ctg      192
Ser His Tyr Gly Met Tyr Trp Val Arg Gln Ala Pro Gly Lys Gly Leu
    50                  55                  60
```

```
gag tgg gtg gca gtt ata tgg tat gat gga agt tat gaa tac aat gca    240
Glu Trp Val Ala Val Ile Trp Tyr Asp Gly Ser Tyr Glu Tyr Asn Ala
 65                  70                  75                  80 gac tcc gtg aag ggc cgg ttc acc atc tcc aga gac aat tcc aag aac    288
Asp Ser Val Lys Gly Arg Phe Thr Ile Ser Arg Asp Asn Ser Lys Asn
             85                  90                  95 acg ctg tat ctg caa atg aac agc ctg aga gcc gag gac acg gct gtg    336
Thr Leu Tyr Leu Gln Met Asn Ser Leu Arg Ala Glu Asp Thr Ala Val
         100                 105                 110 tat tac tgt gcg aga gat agg gtg ggg ctc ttt gac tat tgg ggc cag    384
Tyr Tyr Cys Ala Arg Asp Arg Val Gly Leu Phe Asp Tyr Trp Gly Gln
     115                 120                 125 gga acc ctg gtc acc gtc tcc tca                                    408
Gly Thr Leu Val Thr Val Ser Ser
     130                 135

<210> SEQ ID NO 4
<211> LENGTH: 136
<212> TYPE: PRT
<213> ORGANISM: Homo sapiens

<400> SEQUENCE: 4

Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Thr Ala Ser Gly Phe Thr Phe
         35                  40                  45

Ser His Tyr Gly Met Tyr Trp Val Arg Gln Ala Pro Gly Lys Gly Leu
     50                  55                  60

Glu Trp Val Ala Val Ile Trp Tyr Asp Gly Ser Tyr Glu Tyr Asn Ala
 65                  70                  75                  80

Asp Ser Val Lys Gly Arg Phe Thr Ile Ser Arg Asp Asn Ser Lys Asn
             85                  90                  95

Thr Leu Tyr Leu Gln Met Asn Ser Leu Arg Ala Glu Asp Thr Ala Val
         100                 105                 110

Tyr Tyr Cys Ala Arg Asp Arg Val Gly Leu Phe Asp Tyr Trp Gly Gln
     115                 120                 125

Gly Thr Leu Val Thr Val Ser Ser
     130                 135

<210> SEQ ID NO 5
<211> LENGTH: 287
<212> TYPE: DNA
<213> ORGANISM: Homo sapiens

<400> SEQUENCE: 5
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacc                  287

<210> SEQ ID NO 6
<211> LENGTH: 322
<212> TYPE: DNA
<213> ORGANISM: Homo sapiens
```

<400> SEQUENCE: 6

```
gaaattgtgt tgacgcagtc tccaggcacc ctgtctttgt ctccagggga aagagccacc      60
ctctcctgca gggccagtca gagtattagc agcagctact tagcctggta ccagcagaaa     120
cctggccagg ctcccaggct cctcatctat ggtccatcca gcagggccac tggcatccca     180
gacaggttca gtggcagtgg gtctgggaca gacttcactc tcaccatcag cagactggag     240
cctgaagatt ttgcagtgta ttactgtcag cagtatgctg gctcactcac tttcggccct     300
gggaccaaag tggatatcaa ac                                              322
```

<210> SEQ ID NO 7
<211> LENGTH: 96
<212> TYPE: PRT
<213> ORGANISM: Homo sapiens

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Pro Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Gly Ser Leu
                85                  90                  95

Thr Phe Gly Pro Gly Thr Lys Val Asp Ile Lys
            100                 105

<210> SEQ ID NO 9
<211> LENGTH: 342
<212> TYPE: DNA
<213> ORGANISM: Homo sapiens

<400> SEQUENCE: 9

```
caggtgcagc tggtggagtc tgggggaggc gtggtccagc ctgggaggtc cctgagactc      60
```

```
tcctgtgcag cgtctggatt caccttcagt agctatggca tgcactgggt ccgccaggct    120
ccaggcaagg gctggagtg gtggcagtt atatggtatg atggaagtaa taaatactat      180
gcagactccg tgaagggccg attcaccatc tccagagaca attccaagaa cacgctgtat    240
ctgcaaatga acagcctgag agccgaggac acggctgtgt attactgtgc gagagatact    300
ttgactactg gggccaggga accctggtca ccgtctcctc ag                       342
```

<210> SEQ ID NO 10
<211> LENGTH: 352
<212> TYPE: DNA
<213> ORGANISM: Homo sapiens

<400> SEQUENCE: 10

```
caggtgcaac tggtggagtc tgggggaggc gtggtccagc ctgggaggtc cctgagactc    60
tcctgtacag cgtctggatt caccttcagt cactatggca tgtactgggt ccgccaggct    120
ccaggcaagg gctggagtg gtggcagtt atatggtatg atggaagtta tgaatacaat      180
gcagactccg tgaagggccg gttcaccatc tccagagaca attccaagaa cacgctgtat    240
ctgcaaatga acagcctgag agccgaggac acggctgtgt attactgtgc gagagatagg    300
gtggggctct ttgactattg gggccaggga accctggtca ccgtctcctc ag            352
```

<210> SEQ ID NO 11
<211> LENGTH: 98
<212> TYPE: PRT
<213> ORGANISM: Homo sapiens

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 12
<211> LENGTH: 117
<212> TYPE: PRT
<213> ORGANISM: Homo sapiens

<400> SEQUENCE: 12

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser His Tyr
            20                  25                  30

Gly Met Tyr Trp Val Arg Gln Ala Pro Gly Lys Gly Leu Glu Trp Val
        35                  40                  45

Ala Val Ile Trp Tyr Asp Gly Ser Tyr Glu Tyr Asn Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                        85                  90                  95

Ala Arg Asp Arg Val Gly Leu Phe Asp Tyr Trp Gly Gln Gly Thr Leu
            100                 105                 110

Val Thr Val Ser Ser
            115
```

<210> SEQ ID NO 13
<211> LENGTH: 36
<212> TYPE: DNA
<213> ORGANISM: Homo sapiens

<400> SEQUENCE: 13
agggccagtc agagtattag cagcagctac ttagcc                          36

<210> SEQ ID NO 14
<211> LENGTH: 21
<212> TYPE: DNA
<213> ORGANISM: Homo sapiens

<400> SEQUENCE: 14
ggtccatcca gcagggccac t                                          21

<210> SEQ ID NO 15
<211> LENGTH: 24
<212> TYPE: DNA
<213> ORGANISM: Homo sapiens

<400> SEQUENCE: 15
cagcagtatg ctggctcact cact                                       24

<210> SEQ ID NO 16
<211> LENGTH: 12
<212> TYPE: PRT
<213> ORGANISM: Homo sapiens

<400> SEQUENCE: 16

```
Arg Ala Ser Gln Ser Ile Ser Ser Ser Tyr Leu Ala
 1               5                  10
```

<210> SEQ ID NO 17
<211> LENGTH: 7
<212> TYPE: PRT
<213> ORGANISM: Homo sapiens

<400> SEQUENCE: 17

```
Gly Pro Ser Ser Arg Ala Thr
 1               5
```

<210> SEQ ID NO 18
<211> LENGTH: 8
<212> TYPE: PRT
<213> ORGANISM: Homo sapiens

<400> SEQUENCE: 18

```
Gln Gln Tyr Ala Gly Ser Leu Thr
 1               5
```

<210> SEQ ID NO 19
<211> LENGTH: 15
<212> TYPE: DNA
<213> ORGANISM: Homo sapiens

<400> SEQUENCE: 19
cactatggca tgtac                                              15

<210> SEQ ID NO 20
<211> LENGTH: 51
<212> TYPE: DNA
<213> ORGANISM: Homo sapiens

<400> SEQUENCE: 20
gttatatggt atgatggaag ttatgaatac aatgcagact ccgtgaaggg c       51

<210> SEQ ID NO 21
<211> LENGTH: 24
<212> TYPE: DNA
<213> ORGANISM: Homo sapiens

<400> SEQUENCE: 21
gatagggtgg ggctctttga ctac                                    24

<210> SEQ ID NO 22
<211> LENGTH: 5
<212> TYPE: PRT
<213> ORGANISM: Homo sapiens

<400> SEQUENCE: 22

His Tyr Gly Met Tyr
 1               5

<210> SEQ ID NO 23
<211> LENGTH: 17
<212> TYPE: PRT
<213> ORGANISM: Homo sapiens

<400> SEQUENCE: 23

Val Ile Trp Tyr Asp Gly Ser Tyr Glu Tyr Asn Ala Asp Ser Val Lys
 1               5                  10                  15

Gly

<210> SEQ ID NO 24
<211> LENGTH: 8
<212> TYPE: PRT
<213> ORGANISM: Homo sapiens

<400> SEQUENCE: 24

Asp Arg Val Gly Leu Phe Asp Tyr
 1               5

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caggtkcagc tggtgcagtc                                         20

<210> SEQ ID NO 26
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 26
saggtgcagc tgktggagtc                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaggtgcagc tggtgcagtc                                              20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atggactgga cctggagcat c                                            21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atggaattgg ggctgagctg                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence Synthetic
      primer

<400> SEQUENCE: 30
atggagtttg grctgagctg                                              20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atgaaacacc tgtggttctt c                                            21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
atggggtcaa ccgccatcct                                           20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tgccaggggg aagaccgatg g                                         21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
racatccaga tgayccagtc                                           20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gycatcyrga tgacccagtc                                           20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gatattgtga tgacccagac                                           20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaaattgtgt tgacrcagtc                                           20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 38
gaaatwgtra tgacacagtc                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gatgttgtga tgacacagtc                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gaaattgtgc tgactcagtc                                              20

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cccgctcagc tcctggggct cctg                                         24

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccctgctcag ctcctggggc tgc                                          23

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cccagcgcag cttctcttcc tcctgc                                       26

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 44
atggaaccat ggaagcccca gcacagc                                              27

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cgggaagatg aagacagatg                                                      20

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: any natural amino acid other than Gly
<220> FEATURE:
<221> NAME/KEY: MOD_RES
<222> LOCATION: (5)
<223> OTHER INFORMATION: any natural amino acid other than Ser
<220> FEATURE:
<221> NAME/KEY: MOD_RES
<222> LOCATION: (7)
<223> OTHER INFORMATION: any natural amino acid other than Pro
<220> FEATURE:
<223> OTHER INFORMATION: see specification as filed for detailed
      description of preferred embodiments

<400> SEQUENCE: 46

Gln Gln Tyr Xaa Xaa Ser Xaa Thr
  1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys, Arg or His
<220> FEATURE:
<221> NAME/KEY: MOD_RES
<222> LOCATION: (5)
<223> OTHER INFORMATION: Gly, Ala, Val, Leu or Ile

<400> SEQUENCE: 47

Asp Xaa Val Gly Xaa Phe Asp Tyr
  1               5
```